US012653693B2

(12) United States Patent
   Predick

(10) Patent No.: US 12,653,693 B2
(45) Date of Patent: Jun. 16, 2026

(54) EXPANDABLE IMPLANT ASSEMBLY

(71) Applicant: LIFE SPINE, INC., Huntley, IL (US)

(72) Inventor: Daniel Predick, Wheat Ridge, CO (US)

(73) Assignee: LIFE SPINE, INC., Huntley, IL (US)

(*) Notice: Subject to any disclaimer, the term of this patent is extended or adjusted under 35 U.S.C. 154(b) by 0 days.

(21) Appl. No.: 18/908,080

(22) Filed: Oct. 7, 2024

(65) Prior Publication Data

US 2025/0025315 A1      Jan. 23, 2025

Related U.S. Application Data

(63) Continuation of application No. 18/108,402, filed on Feb. 10, 2023, now Pat. No. 12,138,178, which is a continuation of application No. 16/850,795, filed on Apr. 16, 2020, now Pat. No. 11,602,439.

(51) Int. Cl.
   *A61F 2/44*      (2006.01)
   *A61F 2/30*      (2006.01)

(52) U.S. Cl.
   CPC .. *A61F 2/4425* (2013.01); *A61F 2002/30578* (2013.01); *A61F 2002/443* (2013.01); *A61F 2250/0006* (2013.01); *A61F 2250/0009* (2013.01)

(58) Field of Classification Search
   CPC . A61F 2/4425; A61F 2002/443; A61F 2/4455
   See application file for complete search history.

(56) References Cited

U.S. PATENT DOCUMENTS

| 904,434 | A | 11/1908 | Huff |
| 1,925,385 | A | 9/1933 | Humes |
| 3,846,846 | A | 11/1974 | Fischer |
| 4,466,426 | A | 8/1984 | Blackman |
| 4,636,217 | A | 1/1987 | Ogilvie et al. |

(Continued)

FOREIGN PATENT DOCUMENTS

| CN | 102427769 A | 4/2012 |
| CN | 205866898 U | 1/2017 |

(Continued)

OTHER PUBLICATIONS

International Search Report and Written Opinion for PCT Appl. Ser. No. PCT/US2006/012060 dated Apr. 5, 2007, 4 pages.

(Continued)

*Primary Examiner* — Matthew J Lawson
(74) *Attorney, Agent, or Firm* — Foley & Lardner LLP

(57) ABSTRACT

An expandable implant. The expandable implant includes a base member having a top surface and a bottom surface opposite the top surface, and an adjustable member adjustably coupled to the base member and movable between a first, collapsed position, and a second, expanded position. The adjustable member has a top surface and a bottom surface opposite the top surface. The top surface of the adjustable member and the bottom surface of the base member form a first angle while the adjustable member is in the first, collapsed position, and the top surface of the adjustable member and the bottom surface of the base member form a second angle while the adjustable member is in the second, expanded position. The first angle is different from the second angle.

22 Claims, 26 Drawing Sheets

(56) References Cited

U.S. PATENT DOCUMENTS

| 4,743,256 A | 5/1988 | Brantigan |
|---|---|---|
| 4,863,476 A | 9/1989 | Shepperd |
| 5,098,435 A | 3/1992 | Stednitz et al. |
| 5,192,327 A | 3/1993 | Brantigan |
| 5,236,460 A | 8/1993 | Barber |
| 5,390,683 A | 2/1995 | Pisharodi |
| 5,522,899 A | 6/1996 | Michelson |
| 5,609,635 A | 3/1997 | Michelson |
| 5,645,599 A | 7/1997 | Samani |
| 5,658,335 A | 8/1997 | Allen |
| 5,658,337 A | 8/1997 | Kohrs et al. |
| 5,776,199 A | 7/1998 | Michelson |
| 5,836,948 A | 11/1998 | Zucherman et al. |
| 5,860,977 A | 1/1999 | Zucherman et al. |
| 5,876,404 A | 3/1999 | Zucherman et al. |
| 6,045,579 A | 4/2000 | Hochshuler et al. |
| 6,048,342 A | 4/2000 | Zucherman et al. |
| 6,068,630 A | 5/2000 | Zucherman et al. |
| 6,074,390 A | 6/2000 | Zucherman et al. |
| 6,080,193 A | 6/2000 | Hochshuler et al. |
| 6,113,638 A | 9/2000 | Williams et al. |
| 6,126,689 A | 10/2000 | Brett |
| 6,129,763 A | 10/2000 | Chauvin et al. |
| 6,176,882 B1 | 1/2001 | Biedermann et al. |
| 6,183,471 B1 | 2/2001 | Zucherman et al. |
| 6,190,387 B1 | 2/2001 | Zucherman et al. |
| 6,235,030 B1 | 5/2001 | Zucherman et al. |
| 6,290,724 B1 | 9/2001 | Marino |
| 6,302,914 B1 | 10/2001 | Michelson |
| 6,375,682 B1 | 4/2002 | Fleischmann et al. |
| 6,409,766 B1 | 6/2002 | Brett |
| 6,443,989 B1 | 9/2002 | Jackson |
| 6,443,990 B1 | 9/2002 | Aebi et al. |
| 6,447,544 B1 | 9/2002 | Michelson |
| 6,451,019 B1 | 9/2002 | Zucherman et al. |
| 6,491,724 B1 | 12/2002 | Ferree |
| 6,494,883 B1 | 12/2002 | Ferree |
| 6,537,320 B1 | 3/2003 | Michelson |
| 6,576,016 B1 | 6/2003 | Hochshuler et al. |
| 6,613,091 B1 | 9/2003 | Zdeblick et al. |
| 6,641,614 B1 | 11/2003 | Wagner et al. |
| 6,648,917 B2 | 11/2003 | Gerbec et al. |
| 6,685,742 B1 | 2/2004 | Jackson |
| 6,695,842 B2 | 2/2004 | Zucherman et al. |
| 6,699,246 B2 | 3/2004 | Zucherman et al. |
| 6,699,247 B2 | 3/2004 | Zucherman et al. |
| 6,706,070 B1 | 3/2004 | Wagner et al. |
| 6,752,832 B2 | 6/2004 | Neumann |
| 6,773,460 B2 | 8/2004 | Jackson |
| 6,796,983 B1 | 9/2004 | Zucherman et al. |
| 6,800,092 B1 | 10/2004 | Williams et al. |
| 6,849,093 B2 | 2/2005 | Michelson |
| 7,001,385 B2 | 2/2006 | Bonutti |
| 7,048,736 B2 | 5/2006 | Robinson et al. |
| 7,087,055 B2 | 8/2006 | Lim et al. |
| 7,101,375 B2 | 9/2006 | Zucherman et al. |
| 7,214,243 B2 | 5/2007 | Taylor |
| 7,217,291 B2 | 5/2007 | Zucherman et al. |
| 7,220,280 B2 | 5/2007 | Kast et al. |
| 7,250,055 B1 | 7/2007 | Vanderwalle |
| 7,473,276 B2 | 1/2009 | Aebi et al. |
| 7,503,933 B2 | 3/2009 | Michelson |
| 7,621,950 B1 | 11/2009 | Globerman et al. |
| 7,695,513 B2 | 4/2010 | Zucherman et al. |
| 7,722,674 B1 | 5/2010 | Grotz |
| 7,727,280 B2 | 6/2010 | McLuen |
| 7,731,751 B2 | 6/2010 | Butler et al. |
| 7,789,914 B2 | 9/2010 | Michelson |
| D626,233 S | 10/2010 | Cipoletti et al. |
| 7,824,427 B2 | 11/2010 | Perez-Cruet et al. |
| 7,828,849 B2 | 11/2010 | Lim |
| 7,837,734 B2 | 11/2010 | Zucherman et al. |
| 7,846,188 B2 | 12/2010 | Moskowitz et al. |
| 7,850,733 B2 | 12/2010 | Baynham et al. |
| 7,854,766 B2 | 12/2010 | Moskowitz et al. |
| 7,867,277 B1 | 1/2011 | Tohmeh |
| 7,879,098 B1 | 2/2011 | Simmons, Jr. |
| 7,942,903 B2 | 5/2011 | Moskowitz et al. |
| 7,959,675 B2 | 6/2011 | Gately |
| 7,972,363 B2 | 7/2011 | Moskowitz et al. |
| 8,016,861 B2 | 9/2011 | Mitchell et al. |
| 8,021,430 B2 | 9/2011 | Michelson |
| 8,025,697 B2 | 9/2011 | Abdelgany |
| 8,048,117 B2 | 11/2011 | Zucherman et al. |
| 8,062,375 B2 | 11/2011 | Glerum et al. |
| 8,070,817 B2 | 12/2011 | Gradl et al. |
| 8,071,007 B1 | 12/2011 | Teoh et al. |
| 8,105,382 B2 | 1/2012 | Olmos et al. |
| 8,187,332 B2 | 5/2012 | Mcluen |
| 8,231,656 B2 | 7/2012 | Lee et al. |
| 8,241,330 B2 | 8/2012 | Lamborne et al. |
| 8,241,364 B2 | 8/2012 | Hansell et al. |
| 8,252,060 B2 | 8/2012 | Hansell et al. |
| 8,257,370 B2 | 9/2012 | Moskowitz et al. |
| 8,267,939 B2 | 9/2012 | Cipoletti et al. |
| 8,303,663 B2 | 11/2012 | Jimenez et al. |
| 8,308,804 B2 | 11/2012 | Krueger |
| 8,343,190 B1 | 1/2013 | Mueller et al. |
| 8,353,913 B2 | 1/2013 | Moskowitz et al. |
| 8,353,963 B2 | 1/2013 | Glerum |
| 8,366,777 B2 | 2/2013 | Matthis et al. |
| 8,382,801 B2 | 2/2013 | Lamborne et al. |
| 8,382,842 B2 | 2/2013 | Greenhalgh et al. |
| 8,388,686 B2 | 3/2013 | Aebi et al. |
| 8,394,129 B2 | 3/2013 | Lopez et al. |
| 8,398,713 B2 | 3/2013 | Weiman |
| 8,425,607 B2 | 4/2013 | Waugh et al. |
| 8,435,298 B2 | 5/2013 | Weiman |
| 8,444,696 B2 | 5/2013 | Michelson |
| 8,454,706 B2 | 6/2013 | De Beaubien |
| 8,491,659 B2 | 7/2013 | Weiman |
| 8,506,629 B2 | 8/2013 | Weiland |
| 8,518,120 B2 | 8/2013 | Glerum et al. |
| 8,523,944 B2 | 9/2013 | Jimenez et al. |
| 8,529,628 B2 | 9/2013 | Marino et al. |
| 8,535,380 B2 | 9/2013 | Greenhalgh et al. |
| 8,551,173 B2 | 10/2013 | Lechmann et al. |
| 8,556,979 B2 | 10/2013 | Glerum et al. |
| 8,568,481 B2 | 10/2013 | Olmos et al. |
| 8,597,360 B2 | 12/2013 | Mcluen et al. |
| 8,628,577 B1 | 1/2014 | Jimenez |
| 8,628,578 B2 | 1/2014 | Miller et al. |
| 8,632,595 B2 | 1/2014 | Weiman |
| 8,641,764 B2 | 2/2014 | Gately |
| 8,641,766 B2 | 2/2014 | Donner et al. |
| 8,663,331 B2 | 3/2014 | Mcclellan et al. |
| 8,663,332 B1 | 3/2014 | To et al. |
| 8,679,183 B2 | 3/2014 | Glerum et al. |
| 8,685,098 B2 | 4/2014 | Glerum et al. |
| 8,690,883 B2 | 4/2014 | Collins et al. |
| 8,702,798 B2 | 4/2014 | Matthis et al. |
| 8,709,086 B2 | 4/2014 | Glerum |
| 8,734,516 B2 | 5/2014 | Moskowitz et al. |
| 8,795,366 B2 | 8/2014 | Varela |
| 8,821,506 B2 | 9/2014 | Mitchell |
| 8,845,728 B1 | 9/2014 | Abdou |
| 8,845,731 B2 | 9/2014 | Weiman |
| 8,845,732 B2 | 9/2014 | Weiman |
| 8,845,734 B2 | 9/2014 | Weiman |
| 8,852,279 B2 | 10/2014 | Weiman |
| 8,858,638 B2 | 10/2014 | Michelson |
| 8,864,833 B2 | 10/2014 | Glerum et al. |
| 8,888,853 B2 | 11/2014 | Glerum et al. |
| 8,888,854 B2 | 11/2014 | Glerum et al. |
| 8,894,711 B2 | 11/2014 | Varela |
| 8,894,712 B2 | 11/2014 | Varela |
| 8,906,095 B2 | 12/2014 | Christensen et al. |
| 8,926,704 B2 | 1/2015 | Glerum et al. |
| 8,936,641 B2 | 1/2015 | Cain |
| 8,940,052 B2 | 1/2015 | Lechmann et al. |
| 8,974,505 B2 | 3/2015 | Sawa et al. |
| 9,005,293 B2 | 4/2015 | Moskowitz et al. |
| 9,034,041 B2 | 5/2015 | Wolters et al. |
| 9,034,045 B2 | 5/2015 | Davenport et al. |

(56) References Cited

U.S. PATENT DOCUMENTS

| | | | |
|---|---|---|---|
| 9,039,771 B2 | 5/2015 | Glerum et al. |
| 9,044,284 B2 | 6/2015 | Sweeney |
| 9,060,876 B1 | 6/2015 | To et al. |
| 9,101,487 B2 | 8/2015 | Petersheim |
| 9,119,730 B2 | 9/2015 | Glerum et al. |
| 9,125,757 B2 | 9/2015 | Weiman |
| 9,149,367 B2 | 10/2015 | Davenport et al. |
| 9,186,258 B2 | 11/2015 | Davenport et al. |
| 9,186,262 B2 | 11/2015 | Mcluen et al. |
| 9,198,772 B2 | 12/2015 | Weiman |
| 9,204,922 B2 | 12/2015 | Hooven |
| 9,204,972 B2 | 12/2015 | Weiman et al. |
| 9,204,974 B2 | 12/2015 | Glerum et al. |
| 9,211,196 B2 | 12/2015 | Glerum et al. |
| 9,216,095 B2 | 12/2015 | Glerum et al. |
| 9,216,098 B2 | 12/2015 | Trudeau et al. |
| 9,226,836 B2 | 1/2016 | Glerum |
| 9,233,009 B2 | 1/2016 | Gray et al. |
| 9,278,008 B2 | 3/2016 | Perloff et al. |
| 9,295,562 B2 | 3/2016 | Lechmann et al. |
| 9,301,854 B2 | 4/2016 | Moskowitz et al. |
| 9,333,092 B2 | 5/2016 | To et al. |
| 9,358,123 B2 | 6/2016 | Mcluen et al. |
| 9,358,126 B2 | 6/2016 | Glerum et al. |
| 9,358,128 B2 | 6/2016 | Glerum et al. |
| 9,358,129 B2 | 6/2016 | Weiman |
| 9,364,338 B2 | 6/2016 | Malberg |
| 9,370,434 B2 | 6/2016 | Weiman |
| 9,402,733 B1 | 8/2016 | To et al. |
| 9,402,738 B2 | 8/2016 | Niemiec et al. |
| 9,402,739 B2 | 8/2016 | Weiman et al. |
| 9,408,708 B2 | 8/2016 | Greenhalgh |
| 9,408,717 B2 | 8/2016 | Perrow |
| 9,414,932 B2 | 8/2016 | Errico et al. |
| 9,421,111 B2 | 8/2016 | Baynham |
| 9,433,510 B2 | 9/2016 | Lechmann et al. |
| 9,445,919 B2 * | 9/2016 | Palmatier ............... A61F 2/447 |
| 9,452,063 B2 | 9/2016 | Glerum et al. |
| 9,456,903 B2 | 10/2016 | Glerum et al. |
| 9,456,906 B2 | 10/2016 | Gray et al. |
| 9,463,099 B2 | 10/2016 | Levy et al. |
| 9,474,622 B2 | 10/2016 | Mclaughlin et al. |
| 9,480,579 B2 | 11/2016 | Davenport et al. |
| 9,486,325 B2 | 11/2016 | Davenport et al. |
| 9,486,326 B2 | 11/2016 | Gahman et al. |
| 9,492,286 B2 | 11/2016 | Biedermann et al. |
| 9,492,287 B2 | 11/2016 | Glerum et al. |
| 9,492,289 B2 | 11/2016 | Davenport et al. |
| 9,510,954 B2 | 12/2016 | Glerum et al. |
| 9,517,144 B2 | 12/2016 | Mcatamney et al. |
| 9,532,821 B2 | 1/2017 | Moskowitz et al. |
| 9,532,883 B2 | 1/2017 | Mcluen et al. |
| 9,539,103 B2 | 1/2017 | Mclaughlin et al. |
| 9,539,108 B2 | 1/2017 | Glerum et al. |
| 9,554,918 B2 | 1/2017 | Weiman |
| 9,561,116 B2 | 2/2017 | Weiman et al. |
| 9,561,117 B2 | 2/2017 | Lechmann et al. |
| 9,572,677 B2 | 2/2017 | Davenport et al. |
| 9,579,124 B2 | 2/2017 | Gordon et al. |
| 9,585,765 B2 | 3/2017 | Niemiec et al. |
| 9,597,197 B2 | 3/2017 | Lechmann et al. |
| 9,597,200 B2 | 3/2017 | Glerum et al. |
| 9,603,713 B2 | 3/2017 | Moskowitz et al. |
| 9,610,174 B2 | 4/2017 | Wang et al. |
| 9,622,875 B2 | 4/2017 | Moskowitz et al. |
| 9,622,879 B2 | 4/2017 | Taylor et al. |
| 9,655,737 B2 | 5/2017 | Perloff et al. |
| 9,655,747 B2 | 5/2017 | Glerum et al. |
| 9,662,223 B2 | 5/2017 | Matthis et al. |
| 9,662,224 B2 | 5/2017 | Weiman et al. |
| 9,707,092 B2 | 7/2017 | Davenport et al. |
| 9,770,343 B2 | 9/2017 | Weiman |
| 9,782,265 B2 | 10/2017 | Weiman et al. |
| 9,801,733 B2 | 10/2017 | Wolters et al. |
| 9,814,601 B2 | 11/2017 | Moskowitz et al. |
| 9,833,336 B2 | 12/2017 | Davenport et al. |
| 9,839,528 B2 | 12/2017 | Weiman et al. |
| 9,848,993 B2 | 12/2017 | Moskowitz et al. |
| 9,848,997 B2 | 12/2017 | Glerum et al. |
| 9,848,998 B2 | 12/2017 | Moskowitz et al. |
| 9,855,151 B2 | 1/2018 | Weiman |
| 9,867,719 B2 | 1/2018 | Moskowitz et al. |
| 9,889,022 B2 | 2/2018 | Moskowitz et al. |
| 9,895,238 B2 | 2/2018 | Moskowitz et al. |
| 9,907,673 B2 | 3/2018 | Weiman et al. |
| 9,907,674 B2 | 3/2018 | Moskowitz et al. |
| 9,931,226 B2 | 4/2018 | Kurtaliaj et al. |
| 9,943,418 B2 | 4/2018 | Davenport et al. |
| 9,956,087 B2 | 5/2018 | Seifert et al. |
| 9,962,272 B1 | 5/2018 | Daffinson et al. |
| 9,968,462 B2 | 5/2018 | Weiman |
| 9,974,665 B2 | 5/2018 | Mcluen et al. |
| 9,980,822 B2 | 5/2018 | Perloff et al. |
| 9,980,823 B2 | 5/2018 | Matthis et al. |
| 9,987,143 B2 | 6/2018 | Robinson et al. |
| 10,004,607 B2 | 6/2018 | Weiman et al. |
| 10,016,283 B2 | 7/2018 | Mcluen et al. |
| 10,028,740 B2 | 7/2018 | Moskowitz et al. |
| 10,028,842 B2 | 7/2018 | Gray et al. |
| 10,034,772 B2 | 7/2018 | Glerum et al. |
| 10,034,773 B2 | 7/2018 | Mclaughlin et al. |
| 10,052,213 B2 | 8/2018 | Glerum et al. |
| 10,058,433 B2 | 8/2018 | Lechmann et al. |
| 10,064,742 B2 | 9/2018 | Taylor et al. |
| 10,076,367 B2 | 9/2018 | Moskowitz et al. |
| 10,076,423 B2 | 9/2018 | Miller et al. |
| 10,080,669 B2 | 9/2018 | Davenport et al. |
| 10,085,844 B2 | 10/2018 | Perloff et al. |
| 10,085,849 B2 | 10/2018 | Weiman et al. |
| 10,092,417 B2 | 10/2018 | Weiman et al. |
| 10,092,422 B2 | 10/2018 | Mcluen et al. |
| 10,098,757 B2 | 10/2018 | Logan et al. |
| 10,098,758 B2 | 10/2018 | Matthews et al. |
| 10,098,759 B2 | 10/2018 | Weiman |
| 10,105,239 B2 | 10/2018 | Niemiec et al. |
| 10,111,760 B2 | 10/2018 | Knapp et al. |
| 10,117,754 B2 | 11/2018 | Davenport et al. |
| 10,137,001 B2 | 11/2018 | Weiman |
| 10,137,007 B2 | 11/2018 | Dewey et al. |
| 10,143,500 B2 | 12/2018 | Niemiec et al. |
| 10,143,569 B2 | 12/2018 | Weiman et al. |
| 10,154,911 B2 | 12/2018 | Predick et al. |
| 10,159,583 B2 | 12/2018 | Dietzel et al. |
| 10,195,050 B2 | 2/2019 | Palmatier et al. |
| 10,213,321 B2 | 2/2019 | Knapp et al. |
| 10,219,913 B2 | 3/2019 | Matthews et al. |
| 10,226,359 B2 | 3/2019 | Glerum et al. |
| 10,251,643 B2 | 4/2019 | Moskowitz et al. |
| 10,285,819 B2 | 5/2019 | Greenhalgh |
| 10,285,820 B2 | 5/2019 | Greenhalgh |
| 10,292,828 B2 | 5/2019 | Greenhalgh |
| 10,292,830 B2 | 5/2019 | Mcluen et al. |
| 10,299,934 B2 | 5/2019 | Seifert et al. |
| 10,307,268 B2 | 6/2019 | Moskowitz et al. |
| 10,350,085 B2 | 7/2019 | Glerum et al. |
| 10,376,386 B2 | 8/2019 | Moskowitz et al. |
| 10,383,741 B2 | 8/2019 | Butler et al. |
| 10,420,654 B2 | 9/2019 | Logan et al. |
| 10,426,632 B2 | 10/2019 | Butler et al. |
| 10,426,633 B2 | 10/2019 | Moskowitz et al. |
| 10,433,977 B2 | 10/2019 | Lechmann et al. |
| 10,449,058 B2 | 10/2019 | Lechmann et al. |
| 10,470,894 B2 | 11/2019 | Foley et al. |
| 10,478,319 B2 | 11/2019 | Moskowitz et al. |
| 10,512,550 B2 | 12/2019 | Bechtel et al. |
| 10,531,895 B2 | 1/2020 | Weiman et al. |
| 10,575,966 B2 | 3/2020 | Logan et al. |
| 10,617,533 B2 | 4/2020 | Glerum et al. |
| 10,624,761 B2 | 4/2020 | Davenport et al. |
| 10,639,166 B2 | 5/2020 | Weiman et al. |
| 10,682,240 B2 | 6/2020 | Mcluen et al. |
| 10,702,393 B2 | 7/2020 | Davenport et al. |
| 10,709,569 B2 | 7/2020 | Mclaughlin et al. |
| 10,709,571 B2 | 7/2020 | Iott et al. |

(56) References Cited

U.S. PATENT DOCUMENTS

| | | |
|---|---|---|
| 10,709,573 B2 | 7/2020 | Weiman et al. |
| 10,709,574 B2 | 7/2020 | Mcluen et al. |
| 10,722,379 B2 | 7/2020 | Mclaughlin et al. |
| 10,729,560 B2 | 8/2020 | Baker et al. |
| 10,729,562 B2 | 8/2020 | Knapp et al. |
| 10,736,754 B2 | 8/2020 | Mcluen et al. |
| 10,758,367 B2 | 9/2020 | Weiman et al. |
| 10,765,528 B2 | 9/2020 | Weiman et al. |
| 10,772,737 B2 | 9/2020 | Gray et al. |
| 10,779,957 B2 | 9/2020 | Weiman et al. |
| 10,786,364 B2 | 9/2020 | Davenport et al. |
| 10,799,368 B2 | 10/2020 | Glerum et al. |
| 10,835,387 B2 | 11/2020 | Weiman et al. |
| 10,842,644 B2 | 11/2020 | Weiman et al. |
| 10,869,768 B2 | 12/2020 | Weiman et al. |
| 10,874,522 B2 | 12/2020 | Weiman |
| 10,874,523 B2 | 12/2020 | Weiman et al. |
| 10,925,752 B2 | 2/2021 | Weiman |
| 10,940,014 B2 | 3/2021 | Greenhalgh |
| 10,973,649 B2 | 4/2021 | Weiman et al. |
| 11,020,239 B2 | 6/2021 | Miller et al. |
| 11,033,401 B2 | 6/2021 | Shoshtaev |
| 11,051,951 B2 | 7/2021 | Robinson et al. |
| 11,065,128 B2 | 7/2021 | Zappacosta et al. |
| 11,083,584 B2 | 8/2021 | Lauf et al. |
| 11,219,535 B1 | 1/2022 | Hauck |
| 11,234,833 B2 | 2/2022 | Brotman et al. |
| 11,285,014 B1 | 3/2022 | Josse et al. |
| 11,304,817 B2 | 4/2022 | Altarac et al. |
| 11,304,818 B2 | 4/2022 | Butler et al. |
| 11,717,419 B2 | 8/2023 | Altarac et al. |
| 11,806,250 B2 | 11/2023 | Miller et al. |
| 11,857,432 B2 | 1/2024 | Keller et al. |
| 2002/0010472 A1 | 1/2002 | Kuslich et al. |
| 2002/0029084 A1 | 3/2002 | Paul et al. |
| 2002/0091447 A1 | 7/2002 | Shimp et al. |
| 2002/0128716 A1 | 9/2002 | Cohen et al. |
| 2002/0143343 A1 | 10/2002 | Castro |
| 2002/0143399 A1 | 10/2002 | Sutcliffe |
| 2002/0147461 A1 | 10/2002 | Aldrich et al. |
| 2002/0177897 A1 | 11/2002 | Michelson |
| 2003/0004576 A1 | 1/2003 | Thalgott |
| 2003/0040746 A1 | 2/2003 | Mitchell et al. |
| 2003/0040802 A1 | 2/2003 | Errico et al. |
| 2003/0176926 A1 | 9/2003 | Boehm et al. |
| 2003/0236520 A1 | 12/2003 | Lim et al. |
| 2004/0073213 A1 | 4/2004 | Serhan et al. |
| 2004/0153156 A1 | 8/2004 | Cohen et al. |
| 2004/0167625 A1 | 8/2004 | Beyar et al. |
| 2004/0204747 A1 | 10/2004 | Kemeny et al. |
| 2004/0225292 A1 | 11/2004 | Sasso et al. |
| 2004/0230309 A1 | 11/2004 | Dimauro et al. |
| 2004/0254643 A1 | 12/2004 | Jackson |
| 2005/0027362 A1 | 2/2005 | Williams et al. |
| 2005/0033437 A1 | 2/2005 | Bao et al. |
| 2005/0070911 A1 | 3/2005 | Carrison et al. |
| 2005/0107800 A1 | 5/2005 | Frankel et al. |
| 2005/0119747 A1 | 6/2005 | Fabris Monterumici |
| 2005/0131536 A1 | 6/2005 | Eisermann et al. |
| 2005/0143827 A1 | 6/2005 | Globerman et al. |
| 2005/0177235 A1 | 8/2005 | Baynham et al. |
| 2005/0177236 A1 | 8/2005 | Mathieu et al. |
| 2005/0222681 A1 | 10/2005 | Richley et al. |
| 2005/0228391 A1 | 10/2005 | Levy et al. |
| 2005/0261769 A1 | 11/2005 | Moskowitz et al. |
| 2005/0278036 A1 | 12/2005 | Leonard et al. |
| 2006/0030943 A1 | 2/2006 | Peterman |
| 2006/0036258 A1 | 2/2006 | Zucherman et al. |
| 2006/0084988 A1 | 4/2006 | Kim |
| 2006/0089715 A1 | 4/2006 | Truckai et al. |
| 2006/0089718 A1 | 4/2006 | Zucherman et al. |
| 2006/0095136 A1 | 5/2006 | Mcluen |
| 2006/0122701 A1 | 6/2006 | Kiester |
| 2006/0189999 A1 | 8/2006 | Zwirkoski |
| 2006/0241601 A1 | 10/2006 | Trautwein et al. |
| 2006/0241621 A1 | 10/2006 | Moskowitz et al. |
| 2006/0253201 A1 | 11/2006 | Mcluen |
| 2006/0264938 A1 | 11/2006 | Zucherman et al. |
| 2006/0265077 A1 | 11/2006 | Zwirkoski |
| 2007/0072475 A1 | 3/2007 | Justin et al. |
| 2007/0142915 A1 | 6/2007 | Altarac et al. |
| 2007/0213739 A1 | 9/2007 | Michelson |
| 2007/0244485 A1 | 10/2007 | Greenhalgh et al. |
| 2007/0270968 A1 | 11/2007 | Baynham et al. |
| 2008/0114367 A1 | 5/2008 | Meyer |
| 2008/0114453 A1 | 5/2008 | Francis |
| 2008/0114456 A1 | 5/2008 | Dewey et al. |
| 2008/0119853 A1 | 5/2008 | Felt et al. |
| 2008/0119945 A1 | 5/2008 | Frigg |
| 2008/0140085 A1 | 6/2008 | Gately et al. |
| 2008/0140207 A1 | 6/2008 | Olmos et al. |
| 2008/0147193 A1 | 6/2008 | Matthis et al. |
| 2008/0161818 A1 | 7/2008 | Kloss et al. |
| 2008/0177391 A1 | 7/2008 | Mitchell et al. |
| 2008/0183211 A1 | 7/2008 | Lamborne et al. |
| 2008/0243251 A1 | 10/2008 | Stad et al. |
| 2008/0288077 A1 | 11/2008 | Reo et al. |
| 2008/0312741 A1 | 12/2008 | Lee et al. |
| 2009/0005872 A1 | 1/2009 | Moumene et al. |
| 2009/0062833 A1 | 3/2009 | Song |
| 2009/0062915 A1 | 3/2009 | Kohm et al. |
| 2009/0105832 A1 | 4/2009 | Allain et al. |
| 2009/0192553 A1 | 7/2009 | Maguire et al. |
| 2009/0198338 A1 | 8/2009 | Phan |
| 2009/0198339 A1 | 8/2009 | Kleiner et al. |
| 2009/0222099 A1 | 9/2009 | Liu et al. |
| 2009/0222100 A1 | 9/2009 | Cipoletti et al. |
| 2009/0228109 A1 | 9/2009 | Pointillant et al. |
| 2009/0312837 A1 | 12/2009 | Eisermann et al. |
| 2010/0082109 A1 | 4/2010 | Greenhalgh et al. |
| 2010/0103344 A1 | 4/2010 | Wang et al. |
| 2010/0179655 A1 | 7/2010 | Hansell et al. |
| 2010/0185291 A1 | 7/2010 | Jimenez et al. |
| 2010/0191336 A1 | 7/2010 | Greenhalgh |
| 2010/0204795 A1 | 8/2010 | Greenhalgh |
| 2010/0211176 A1 | 8/2010 | Greenhalgh |
| 2010/0234889 A1 | 9/2010 | Hess |
| 2010/0241167 A1 | 9/2010 | Taber et al. |
| 2010/0249937 A1 | 9/2010 | Blain et al. |
| 2010/0286777 A1 | 11/2010 | Errico et al. |
| 2011/0022090 A1 | 1/2011 | Gordon et al. |
| 2011/0029085 A1 | 2/2011 | Hynes et al. |
| 2011/0046682 A1 | 2/2011 | Stephan et al. |
| 2011/0054538 A1 | 3/2011 | Zehavi et al. |
| 2011/0066186 A1 | 3/2011 | Boyer et al. |
| 2011/0071635 A1 | 3/2011 | Zhang et al. |
| 2011/0077738 A1 | 3/2011 | Ciupik et al. |
| 2011/0144692 A1 | 6/2011 | Saladin et al. |
| 2011/0144753 A1 | 6/2011 | Marchek et al. |
| 2011/0144755 A1 | 6/2011 | Baynham et al. |
| 2011/0166654 A1 | 7/2011 | Gately |
| 2011/0172709 A1 | 7/2011 | Lyons et al. |
| 2011/0172716 A1 | 7/2011 | Glerum |
| 2011/0172774 A1 | 7/2011 | Varela |
| 2011/0178599 A1 | 7/2011 | Brett |
| 2011/0184468 A1 | 7/2011 | Metcalf et al. |
| 2011/0190817 A1 | 8/2011 | Thommen et al. |
| 2011/0196494 A1 | 8/2011 | Yedlicka et al. |
| 2011/0224731 A1 | 9/2011 | Smisson et al. |
| 2011/0282453 A1 | 11/2011 | Greenhalgh et al. |
| 2011/0301711 A1 | 12/2011 | Palmatier et al. |
| 2011/0319997 A1 | 12/2011 | Glerum et al. |
| 2012/0010717 A1 | 1/2012 | Spann |
| 2012/0016418 A1 | 1/2012 | Chin et al. |
| 2012/0022652 A1 | 1/2012 | Berger et al. |
| 2012/0035730 A1 | 2/2012 | Spann |
| 2012/0046748 A1 | 2/2012 | Weiman |
| 2012/0059472 A1 | 3/2012 | Weiman |
| 2012/0059474 A1 | 3/2012 | Weiman |
| 2012/0059475 A1 | 3/2012 | Weiman |
| 2012/0071978 A1 | 3/2012 | Suedkamp et al. |
| 2012/0109203 A1 | 5/2012 | Dryer et al. |
| 2012/0185049 A1 | 7/2012 | Varela |
| 2012/0203347 A1 | 8/2012 | Glerum et al. |

(56) References Cited

U.S. PATENT DOCUMENTS

| | | |
|---|---|---|
| 2012/0221051 A1 | 8/2012 | Robinson |
| 2012/0226357 A1 | 9/2012 | Varela |
| 2012/0330422 A1 | 12/2012 | Weiman |
| 2013/0023993 A1 | 1/2013 | Weiman |
| 2013/0023994 A1 | 1/2013 | Glerum |
| 2013/0085572 A1 | 4/2013 | Glerum |
| 2013/0103156 A1 | 4/2013 | Packer et al. |
| 2013/0116793 A1 | 5/2013 | Kloss |
| 2013/0144391 A1 | 6/2013 | Siegal et al. |
| 2013/0158663 A1* | 6/2013 | Miller .................. A61F 2/4455 |
| | | 623/17.16 |
| 2013/0158664 A1 | 6/2013 | Palmatier et al. |
| 2013/0158668 A1 | 6/2013 | Nichols et al. |
| 2013/0158669 A1 | 6/2013 | Sungarian et al. |
| 2013/0197647 A1 | 8/2013 | Wolters et al. |
| 2013/0211526 A1 | 8/2013 | Alheidt et al. |
| 2013/0345813 A1 | 12/2013 | Frank et al. |
| 2014/0067071 A1 | 3/2014 | Weiman et al. |
| 2014/0148904 A1 | 5/2014 | Robinson |
| 2014/0163682 A1 | 6/2014 | Lott et al. |
| 2014/0163683 A1 | 6/2014 | Seifert et al. |
| 2014/0188224 A1 | 7/2014 | Dmuschewsky |
| 2014/0236296 A1 | 8/2014 | Wagner et al. |
| 2014/0249629 A1 | 9/2014 | Moskowitz et al. |
| 2014/0249632 A1 | 9/2014 | Weiman |
| 2014/0277461 A1 | 9/2014 | Nebosky et al. |
| 2014/0277473 A1 | 9/2014 | Perrow |
| 2014/0277500 A1 | 9/2014 | Logan et al. |
| 2014/0288653 A1 | 9/2014 | Chen |
| 2014/0343678 A1 | 11/2014 | Suddaby et al. |
| 2015/0012097 A1 | 1/2015 | Ibarra et al. |
| 2015/0066145 A1 | 3/2015 | Rogers et al. |
| 2015/0100126 A1 | 4/2015 | Melkent et al. |
| 2015/0100128 A1 | 4/2015 | Glerum et al. |
| 2015/0100130 A1 | 4/2015 | Perrow |
| 2015/0112438 A1 | 4/2015 | Mclean |
| 2015/0173917 A1 | 6/2015 | Radcliffe et al. |
| 2015/0230931 A1 | 8/2015 | Greenhalgh |
| 2015/0257894 A1 | 9/2015 | Levy et al. |
| 2015/0351928 A1 | 12/2015 | Butler et al. |
| 2015/0374507 A1 | 12/2015 | Wolters et al. |
| 2016/0051377 A1 | 2/2016 | Weiman et al. |
| 2016/0089247 A1 | 3/2016 | Nichols et al. |
| 2016/0095718 A1 | 4/2016 | Weiman et al. |
| 2016/0113776 A1 | 4/2016 | Capote |
| 2016/0120660 A1 | 5/2016 | Melkent et al. |
| 2016/0242927 A1 | 8/2016 | Seifert et al. |
| 2016/0310291 A1 | 10/2016 | Greenhalgh |
| 2016/0361177 A1 | 12/2016 | Biedermann et al. |
| 2016/0367377 A1 | 12/2016 | Faulhaber |
| 2016/0374826 A1 | 12/2016 | Palmatier et al. |
| 2017/0014239 A1 | 1/2017 | Seifert et al. |
| 2017/0014244 A1 | 1/2017 | Seifert et al. |
| 2017/0056197 A1 | 3/2017 | Weiman et al. |
| 2017/0100255 A1 | 4/2017 | Hleihil et al. |
| 2017/0172756 A1* | 6/2017 | Faulhaber ............. A61F 2/4611 |
| 2017/0216036 A1 | 8/2017 | Cordaro |
| 2017/0224504 A1 | 8/2017 | Butler et al. |
| 2017/0224505 A1 | 8/2017 | Butler et al. |
| 2017/0246006 A1 | 8/2017 | Carnes et al. |
| 2017/0258605 A1 | 9/2017 | Blain et al. |
| 2017/0281432 A1 | 10/2017 | Glerum et al. |
| 2017/0296352 A1 | 10/2017 | Richerme et al. |
| 2017/0333198 A1 | 11/2017 | Robinson |
| 2017/0333199 A1* | 11/2017 | Sharifi-Mehr ........ A61F 2/4455 |
| 2017/0333200 A1 | 11/2017 | Arnin |
| 2017/0348116 A1 | 12/2017 | Weiman |
| 2017/0367842 A1 | 12/2017 | Predick et al. |
| 2018/0000609 A1 | 1/2018 | Hessler et al. |
| 2018/0014947 A1 | 1/2018 | Baynham |
| 2018/0042732 A1 | 2/2018 | Seifert et al. |
| 2018/0049885 A1 | 2/2018 | Weiman et al. |
| 2018/0055652 A1 | 3/2018 | Davenport et al. |
| 2018/0185163 A1 | 7/2018 | Weiman et al. |
| 2018/0193160 A1 | 7/2018 | Hsu et al. |
| 2018/0243107 A1 | 8/2018 | Foley et al. |
| 2018/0256359 A1 | 9/2018 | Greenhalgh |
| 2018/0289505 A1 | 10/2018 | Foley et al. |
| 2018/0296361 A1 | 10/2018 | Butler et al. |
| 2018/0303621 A1 | 10/2018 | Brotman et al. |
| 2018/0318101 A1* | 11/2018 | Engstrom ............... A61F 2/447 |
| 2018/0325693 A1 | 11/2018 | Weiman et al. |
| 2018/0360616 A1* | 12/2018 | Luu ........................ A61F 2/4455 |
| 2019/0021871 A1 | 1/2019 | Baynham |
| 2019/0133779 A1 | 5/2019 | Mclaughlin et al. |
| 2019/0133784 A1 | 5/2019 | Gunn et al. |
| 2019/0201210 A1 | 7/2019 | Besaw et al. |
| 2019/0254836 A1* | 8/2019 | Cowan .................... A61F 2/447 |
| 2019/0254838 A1 | 8/2019 | Miller et al. |
| 2019/0298524 A1 | 10/2019 | Lauf et al. |
| 2019/0307577 A1 | 10/2019 | Predick et al. |
| 2019/0314168 A1 | 10/2019 | Faulhaber |
| 2019/0328540 A1 | 10/2019 | Seifert et al. |
| 2019/0374348 A1 | 12/2019 | Butler et al. |
| 2019/0388232 A1 | 12/2019 | Purcell et al. |
| 2019/0388238 A1 | 12/2019 | Lechmann et al. |
| 2020/0054461 A1 | 2/2020 | Marrocco et al. |
| 2020/0129307 A1 | 4/2020 | Hunziker et al. |
| 2020/0360153 A1 | 11/2020 | Weiman et al. |
| 2021/0015627 A1 | 1/2021 | Weiman et al. |
| 2021/0030560 A1 | 2/2021 | Abu-Mulaweh et al. |
| 2021/0045891 A1 | 2/2021 | Rogers et al. |
| 2021/0045892 A1 | 2/2021 | Rogers et al. |
| 2021/0077274 A1* | 3/2021 | Robie .................... A61F 2/4425 |
| 2021/0113349 A1 | 4/2021 | Weiman et al. |
| 2021/0137699 A1* | 5/2021 | Jang ..................... A61F 2/4455 |
| 2021/0259849 A1 | 8/2021 | Robinson et al. |
| 2021/0322181 A1 | 10/2021 | Predick |
| 2021/0353428 A1 | 11/2021 | Predick et al. |
| 2022/0133493 A1 | 5/2022 | Josse et al. |
| 2022/0133495 A1 | 5/2022 | Glerum et al. |
| 2022/0304823 A1 | 9/2022 | Melchor |
| 2022/0387184 A1 | 12/2022 | Josse et al. |

FOREIGN PATENT DOCUMENTS

| | | |
|---|---|---|
| DE | 94 07 806 U1 | 7/1994 |
| DE | 20314708 U1 | 11/2003 |
| DE | 10 2020 200 882 A1 | 7/2020 |
| EP | 0 880 950 A1 | 12/1998 |
| EP | 1 925 272 A1 | 5/2008 |
| EP | 2 777 633 A2 | 9/2014 |
| EP | 3 031 424 A1 | 6/2016 |
| EP | 3 245 982 A1 | 11/2017 |
| EP | 3 366 263 A1 | 8/2018 |
| EP | 3 479 799 A1 | 5/2019 |
| EP | 3 769 725 A1 | 1/2021 |
| FR | 2717068 A1 | 4/1996 |
| FR | 2727003 B1 | 4/1997 |
| FR | 2894130 A1 | 6/2007 |
| GB | 0 284 462 A | 2/1928 |
| KR | 200290058 Y1 | 9/2002 |
| KR | 100905962 B1 | 7/2009 |
| WO | WO-95/31158 A1 | 11/1995 |
| WO | WO-99/26562 A1 | 6/1999 |
| WO | WO-00/44319 A1 | 8/2000 |
| WO | WO-02/44319 A1 | 6/2002 |
| WO | WO-2004/052245 A1 | 6/2004 |
| WO | WO-2005/009299 A1 | 2/2005 |
| WO | WO-2006/102485 A2 | 9/2006 |
| WO | WO-2006/105437 A2 | 10/2006 |
| WO | WO-2009/124269 A1 | 10/2009 |
| WO | WO-2010/148112 A1 | 12/2010 |
| WO | WO-2012/121726 A1 | 9/2012 |
| WO | WO-2014/134590 A1 | 9/2014 |
| WO | WO-2014/165319 A1 | 10/2014 |
| WO | WO-2015/009793 A1 | 1/2015 |
| WO | WO-2015/063721 A1 | 5/2015 |
| WO | WO-2015/085111 A1 | 6/2015 |
| WO | WO-2016/051095 A1 | 4/2016 |
| WO | WO-2016/077610 A1 | 5/2016 |
| WO | WO-2016/127139 A1 | 8/2016 |
| WO | WO-2017/027277 A1 | 2/2017 |
| WO | WO-2017/027873 A1 | 2/2017 |

(56) References Cited

FOREIGN PATENT DOCUMENTS

| | | | |
|---|---|---|---|
| WO | WO-2017/066463 A1 | 4/2017 |
| WO | WO-2017/106614 A1 | 6/2017 |
| WO | WO-2018/049227 A1 | 3/2018 |
| WO | WO-2018/200507 A1 | 11/2018 |
| WO | WO-2018/200530 A1 | 11/2018 |
| WO | WO-2019/014139 A1 | 1/2019 |
| WO | WO-2019/126213 A1 | 6/2019 |
| WO | WO-2019/241687 A1 | 12/2019 |
| WO | WO-2021/030645 A1 | 2/2021 |

OTHER PUBLICATIONS

"MectaLIF Oblique & Posterior Intervertebral Body Fusion Device." Brochure. 2004, Medacta International, San Pietro, Switzerland.

"Webster's II New College Dictionary." Excerpts. 2005, Houghton Mifflin Co., p. 992.

"Wedge." Encyclopedia Brittanica. Aug. 14, 2008. britannica.com/print/article/638734.

Bacfuse® Spinous Process Fusion Plate Surgical Technique, 2011, Pioneer Surgical, 12 pages.

Extended European Search Report for European Application No. 14159101.6, dated Jun. 18, 2014, 6 pages.

Extended European Search Report for European Application No. 16169890.7, dated Oct. 21, 2016, 7 pages.

Folman, et al., "Posterior Lumbar Interbody Fusion for Degenerative Disc Disease Using a Minimally Invasive B-Twin Expandable Spinal Spacer." Journal of Spinal Disorders & Techniques. 2003, vol. 16, No. 5, pp. 455-460.

International Preliminary Report on Patentability in PCT/US2022/053230 dated Jun. 27, 2024 (12 pages).

International Search Report and Written Opinion for PCT Appl. Ser. No. PCT/US2012/057324 dated Dec. 20, 2012, 10 pages.

International Search Report and Written Opinion for PCT Appl. Ser. No. PCT/US2018/029120 dated Jun. 28, 2018, 17 pages.

International Search Report and Written Opinion for PCT Appl. Ser. No. PCT/US2018/029149 dated Jun. 25, 2018, 13 pages.

International Search Report and Written Opinion for PCT Appl. Ser. No. PCT/US2020/036809 dated Sep. 14, 2020, 12 pages.

International Search Report and Written Opinion for PCT Appl. Ser. No. PCT/US2020/037020 dated Sep. 29, 2020, 20 pages.

International Search Report and Written Opinion for PCT Appl. Ser. No. PCT/US2021/026606 dated Jul. 15, 2021, 20 pages.

International Search Report and Written Opinion for PCT Appl. Ser. No. PCT/US2021/026610 dated Jul. 20, 2021, 18 pages.

International Search Report and Written Opinion for PCT Appl. Ser. No. PCT/US2021/030261 dated Aug. 31, 2021, 18 pages.

International Search Report and Written Opinion for PCT Appl. Ser. No. PCT/US2021/031596 dated Sep. 28, 2021, 12 pages.

International Search Report and Written Opinion for PCT Appl. Ser. No. PCT/US2021/033832 dated Sep. 17, 2021, 18 pages.

International Search Report and Written Opinion for PCT Appl. Ser. No. PCT/US2022/053230 dated May 3, 2023, 18 pages.

International Search Report and Written Opinion for PCT Appl. Ser. No. PCT/US2023/021528 dated Aug. 24, 2023 , 17 pages.

Kambin, P., et al., "Arthroscopic Discectomy of the Lumbar Spine." Clinical Orthopaedics and Related Research. Apr. 1997, No. 337, pp. 49-57.

Kim, D., et al. "Posterior Lumbar Interbody Fusion Using a Unilateral Single Cage and a Local Morselized Bone Graft in the Degenerative Lumbar Spine." Clinics in Orthopedic Surgery. 2009, vol. 1, No. 4, pp. 214-221.

Kim, Y, et al., "Clinical Applications of the Tubular Retractor on Spinal Disorders." Journal of Korean Neurosurgery, Nov. 2007, No. 42, pp. 244-250.

Moore, J., et al., "Mechanics Map—Wedges." Aug. 20, 2022, mechanicsmap.psu.edu/websites/7_friction/7-3_wedges/wedges.

Peltier, L. "Orthopedics: A History and Iconography" 1993, Norman Publishing, San Francisco, CA.

Sasso, R., et al., "Anterior Lumbar Interbody Fusion." Surgical Management of Low Back Pain. 2009, Chapter 10, pp. 87-95.

Schizas, C., "Spinal Fusion: Techniques Results and Limitations." European Cells and Materials. 2005, vol. 10, Suppl. 3, p. 1.

Search Report for International Application No. PCT/US2018/041306, mail date Sep. 28, 2018, 12 pages.

Tsuang, Y., et al., "Comparison of cage application modality in posterior lumbar interbody fusion with posterior instrumentation—A finite element study." Medical Engineering & Physics 31. 2009, pp. 565-570.

Virk, S., et al. "History of Spinal Fusion: Where We Came from and Where We Are Going." Current Concepts in Spinal Fusion. HSS Journal, 2020, No. 16, pp. 137-142.

Xiao, Y, et al., "Unilateral Transforaminal Lumbar Interbody Fusion: a Review of the Technique, Indications and Graft Materials." The Journal of International Medical Research. 2009, No. 37, pp. 908-917.

* cited by examiner

EXPANDABLE IMPLANT ASSEMBLY

CROSS REFERENCE TO RELATED APPLICATIONS

This application is a continuation of U.S. patent application Ser. No. 18/108,402, filed Feb. 10, 2023, which is a continuation of U.S. patent application Ser. No. 16/850,795, filed Apr. 16, 2020, the disclosures of which are incorporated herein by reference.

BACKGROUND

The present disclosure relates to expandable implants and devices, including spinal interbody and intravertebral body devices, and vertebral interbody and intravertebral devices that are expandable after spinal placement thereof.

Many people contend with spine issues as a result of age, disease, and trauma, as well as congenital and acquired complications and conditions. While some of these issues can be alleviated without surgery, other issues necessitate surgery. Spinal fusion may be recommended for conditions such as spondylolistheses, degenerative disc disease, or recurrent disc herniation, and is designed to create solid bone between adjacent vertebrae, thereby eliminating any movement between the bones. A spinal fusion uses an implant or device known as an interbody cage or spacer along with bone graft and/or bone graft substitute that is inserted into the disc space between adjacent vertebrae from one side of the spine. Typically, additional surgical hardware (implants) such as pedicle screws and rods or plates are attached to the back of the vertebrae. As the bone graft heals, it fuses the adjacent vertebrae to form one long vertebra.

Fusion cages, as well as other types of implants, bodies and/or devices, are frequently utilized in spinal surgery inside a vertebra (intravertebral) and/or between vertebrae of a patient (interbody), or adjacent other bone bodies. With interbody devices, one or more such spinal bodies are placed between vertebrae to provide support and promote fusion between adjacent vertebrae where such is necessary due to disease, injury, general deterioration or congenital problem. With intravertebral devices, one or more spinal bodies are placed within a vertebra.

Spinal devices, such as fusion cages and/or the like, are inserted into a spinal space either anteriorly, posteriorly, laterally or posterolaterally.

SUMMARY

In some embodiments, an expandable implant is disclosed. The expandable implant includes a base member having a top surface and a bottom surface opposite the top surface, and an adjustable member adjustably coupled to the base member and movable between a first, collapsed position, and a second, expanded position. The adjustable member has a top surface and a bottom surface opposite the top surface. The top surface of the adjustable member and the bottom surface of the base member form a first angle while the adjustable member is in the first, collapsed position, and the top surface of the adjustable member and the bottom surface of the base member form a second angle while the adjustable member is in the second, expanded position. The first angle is different from the second angle.

In further embodiments, an expandable implant is disclosed. The expandable implant includes a base member having a guide groove and an adjustable member adjustably coupled to the base member and movable between a first, collapsed position, and a second, expanded position, wherein the adjustable member has a guide rail. The guide groove is configured to receive the guide rail, such that the guide rail translates within the guide groove as the adjustable member is moved from the first, collapsed position to the second, expanded position. The guide rail has a curvature such that the adjustable member moves in a non-linear manner from the first, collapsed position to the second, expanded position.

In further embodiments, an expandable implant is disclosed. The expandable implant includes a plurality of anchoring members, a base member configured to receive an anchoring member, an adjustable member adjustably coupled to the base member and movable between a first, collapsed position, and a second, expanded position, wherein the adjustable member is configured to receive an anchoring member, and a control assembly including a control shaft.

Rotation of the control shaft causes relative movement of the adjustable member relative to the base member.

BRIEF DESCRIPTION OF THE FIGURES

The features of the subject matter disclosed herein will be better understood by reference to the accompanying drawings which illustrate the subject matter disclosed herein, wherein.

Figure 1:
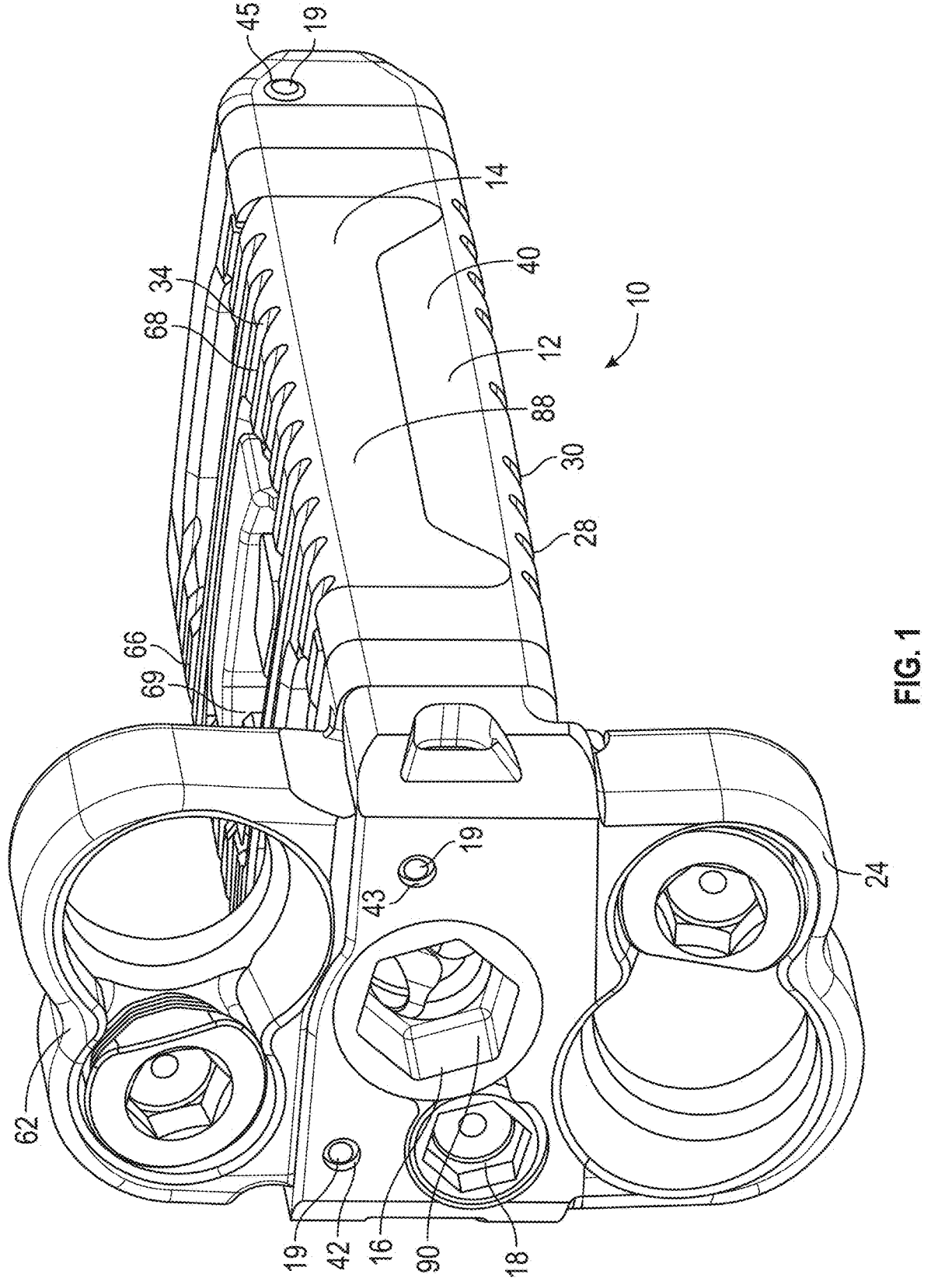
FIG. 1 is a perspective view of an implant in a collapsed position according to an example embodiment.
Figure 2:
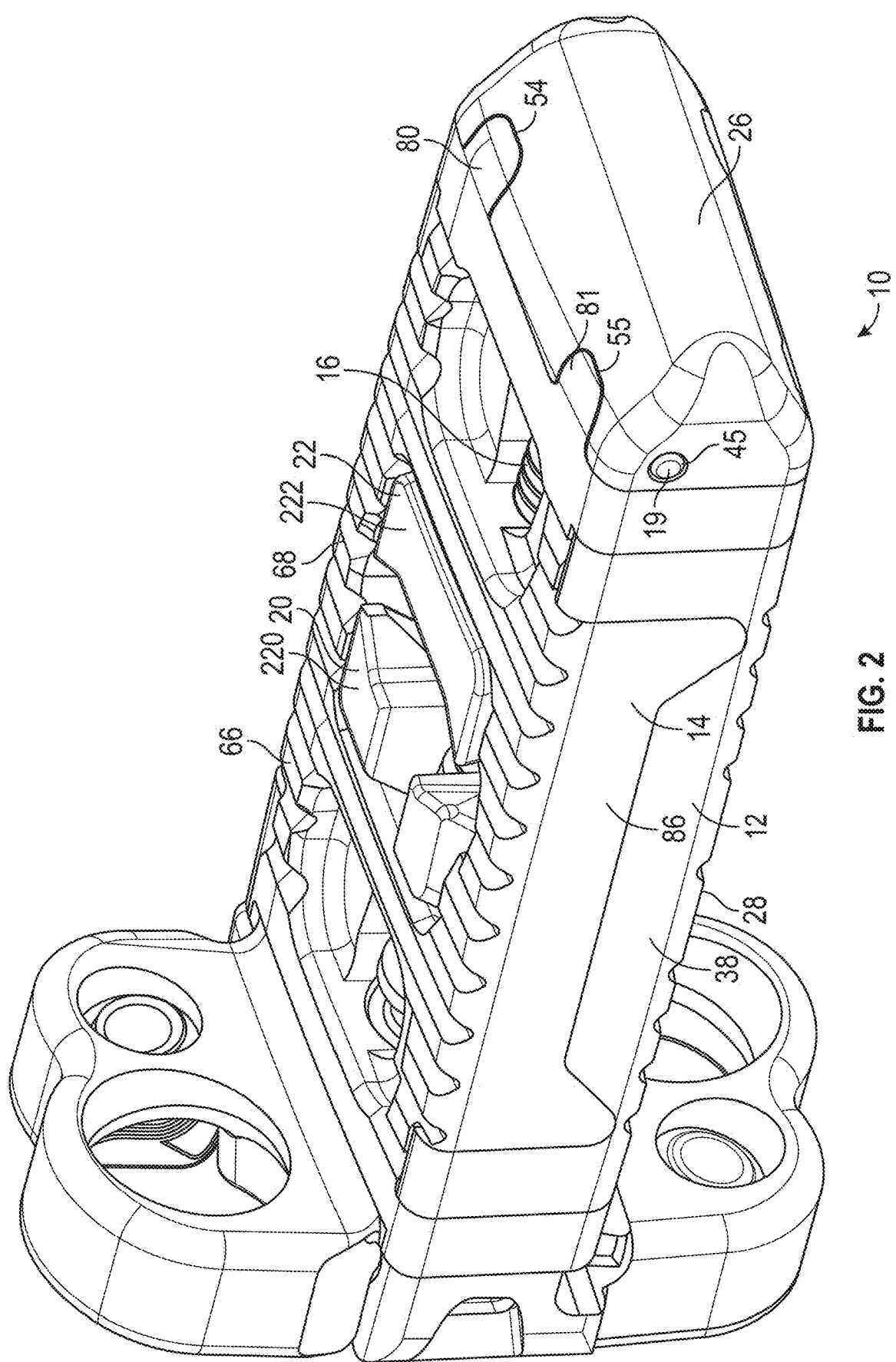
FIG. 2 is another perspective view of the implant of FIG. 1 in a collapsed position according to an example embodiment.

Corresponding reference characters indicate corresponding parts throughout the several views. Although the drawings represent embodiments of the disclosure, the drawings are not necessarily to scale and certain features may be exaggerated in order to better illustrate and explain the principles of the present disclosure. The exemplifications set out herein illustrate several embodiments, but the exemplifications are not to be construed as limiting the scope of the disclosure in any manner.

DETAILED DESCRIPTION

Before turning to the figures, which illustrate certain exemplary embodiments in detail, it should be understood that the present disclosure is not limited to the details or methodology set forth in the description or illustrated in the figures. It should also be understood that the terminology used herein is for the purpose of description only and should not be regarded as limiting.

The present disclosure relates to expandable and/or dynamic implants. In an example embodiment, the implant may be an interbody (between adjacent vertebrae), intravertebral-body (inside the vertebrae) and/or spinal stabilization devices that may or may not be used as interbody fusion cages or devices, interbody/intravertebral bodies/body stabilization devices and/or the like (e.g., spinal device(s)) for providing support, stabilization and/or promoting bone growth between or inside vertebrae or other portions of bone that have been destabilized or otherwise due to injury, illness and/or the like. Particularly, the present disclosure provides various versions of dynamic (expandable and/or expandable and retractable) interbody/intravertebral body devices that are usable in a spinal column or other areas of a human.

Various embodiments disclosed herein are directed to expandable implants that are implantable between adjacent bodies of bone. For example, the implant may be implanted or inserted into a human spine adjacent upper and lower vertebrae of the spine. According to various exemplary embodiments, the components of the implants disclosed herein may be made of any suitable material(s), including a variety of metals, plastics, composites, or other suitable bio-compatible materials. In some embodiments, one or more components of the implants disclosed herein may be made of the same material, while in other embodiments, different materials may be used for different components of the various implants.

Referring now to FIGS. 1-4, an expandable implant 10 is shown according to an exemplary embodiment. The implant 10 is usable, for example, between and/or within vertebral bodies of the spine. It should be understood that the implant 10 may in some embodiments be usable in other portions of the body in addition to the spine, and all such applications are to be understood to be within the scope of the present disclosure.

According to some embodiments, the implant 10 includes a base member 12 and an adjustable member 14 adjustably coupled to the base member 12. The implant 10 may further include a control shaft 16 received by the base member 12 retained by a cam screw 18 passing through a portion of the base member 12. A first control member 20 and a second control member 22 are received on the control shaft 16 and are movable along the control shaft 16 to adjust a position of the adjustable member 14 between a collapsed position, as shown in FIGS. 1-4, and an expanded position, as shown in FIGS. 5-8.

Figure 18:
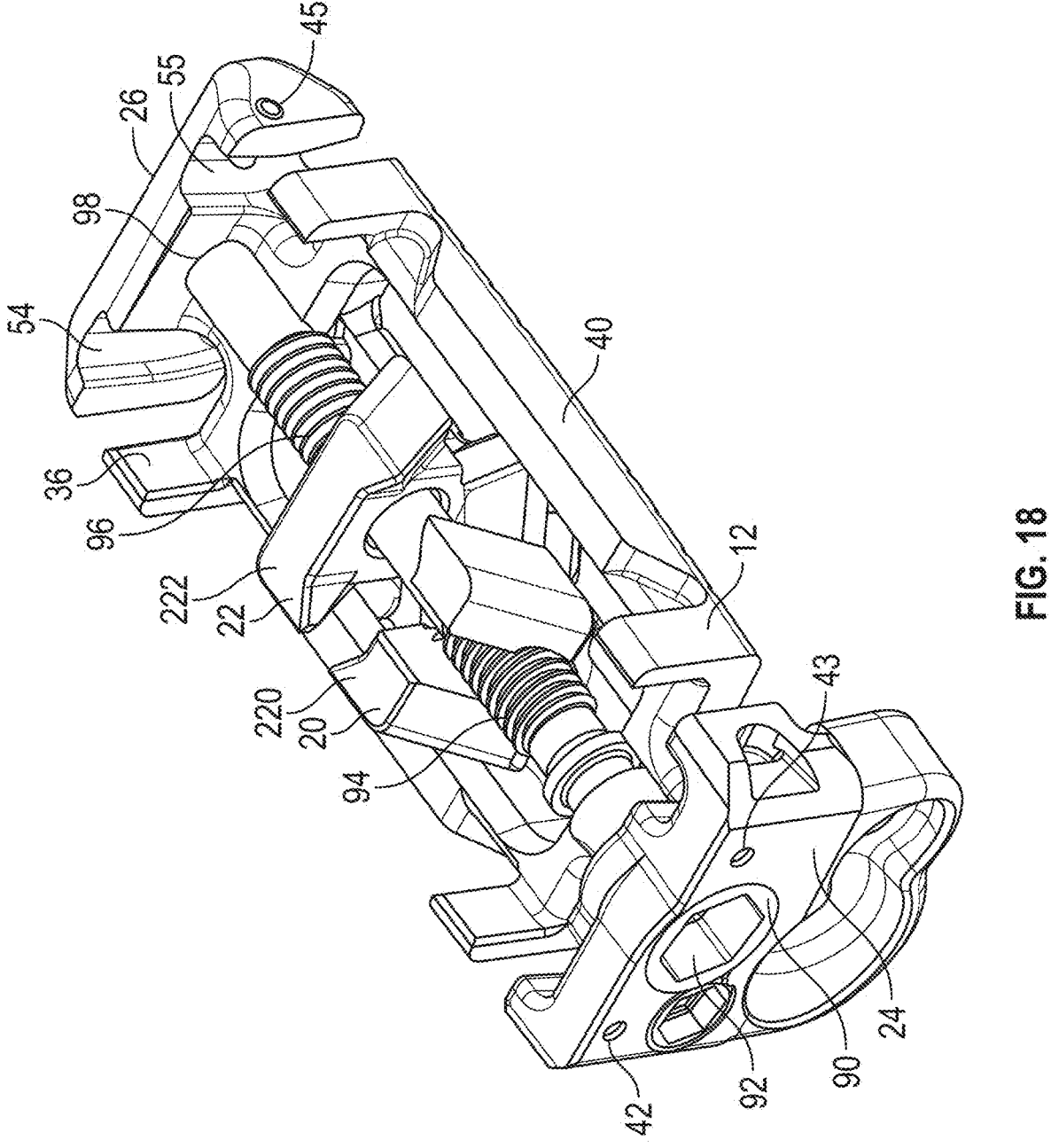
FIG. 18 is a perspective view of a control shaft and control members within a base member of the implant of FIG. 1 according to an example embodiment.

As shown in FIG. 18, the base member 12 includes a front or first end 24, a rear or second end 26, and a central cavity 36 disposed between the first end 24 and the second end 26. The base member 12 further includes a bottom surface 28 having ridges or projections 30 formed by corresponding grooves, a top surface 32 opposite the bottom surface 28, a first side 38, and a second side 40. The projections 30 are configured to engage adjacent portions of bone. In some embodiments, the front end 24 includes a first pin aperture 42 configured to receive a retention pin 19 and a second pin aperture 43 configured to receive a retention pin 19. In some embodiments, the first side 38 includes a third pin aperture, and the second side 40 includes a fourth pin aperture 45 configured to receive a retention pin 19. In some embodiments, such as the embodiment shown in FIG. 1, the first side 38 does not include a third pin aperture. The first pin aperture 42, second pin aperture 43, third pin aperture, and fourth pin aperture 45 may be configured to individually receive a retention pin 19 (e.g. in a press fit or other manner of retention). The first end 24 of the base member 12 includes a control bore 48 (see FIG. 9) configured to receive a first portion of the control shaft 16. The second end 26 includes a tip bore 50 (see FIG. 7) configured to receive a head 90 of the control shaft 16.

Figure 19:
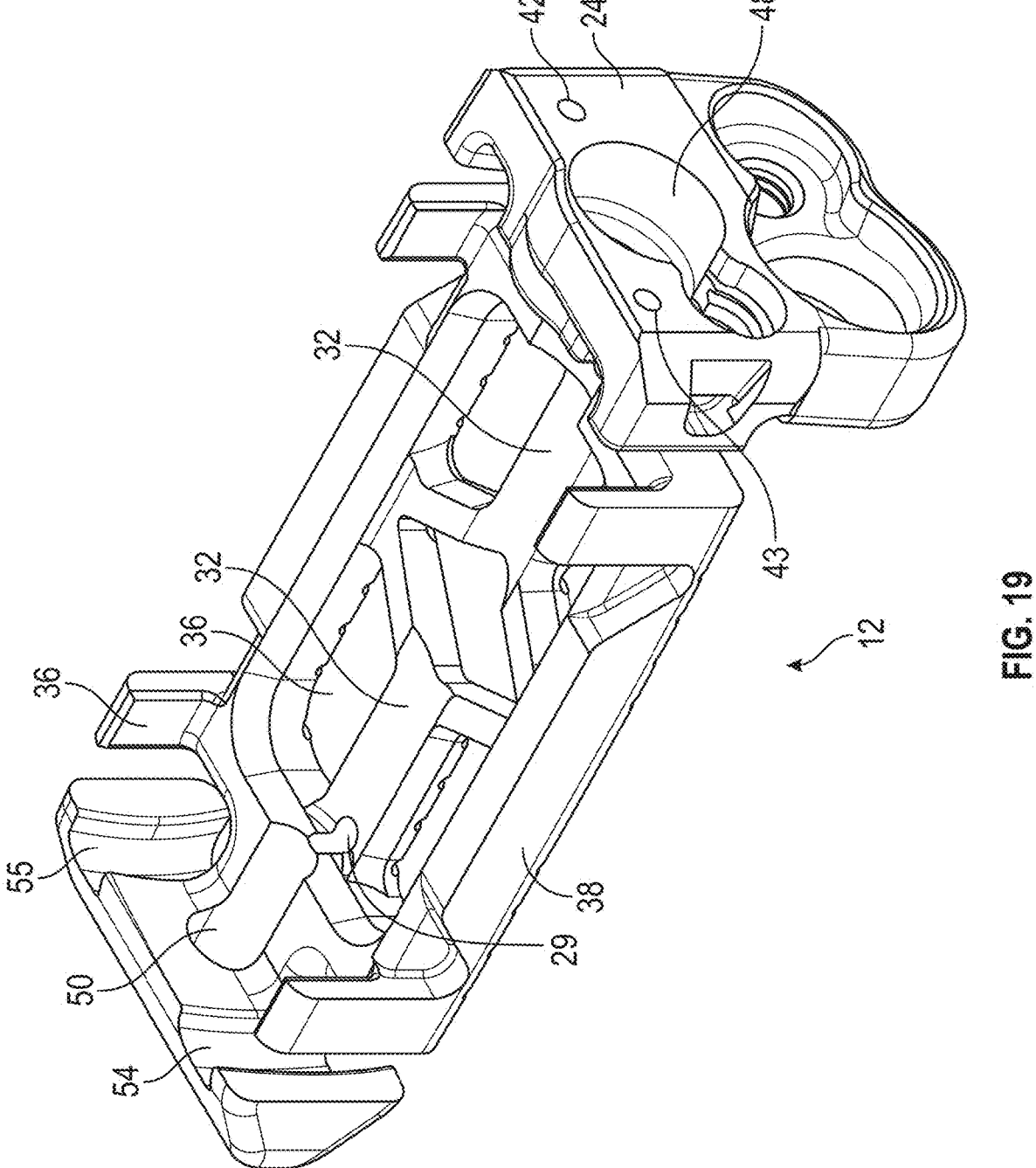
FIG. 19 is a perspective view of a base member of the implant of FIG. 1 according to an example embodiment.
Figure 20:
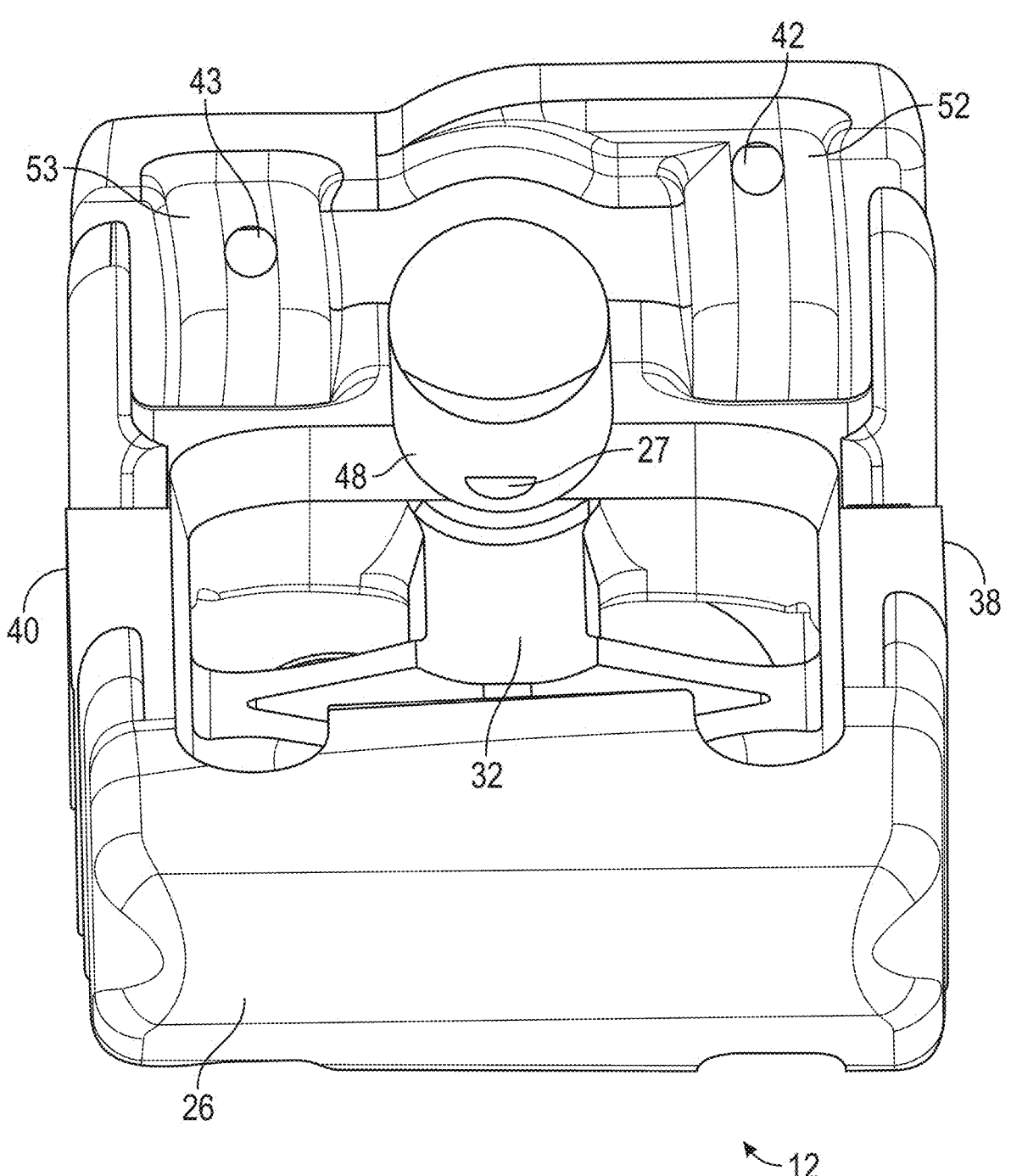
FIG. 20 is a rear perspective view of the base member of FIG. 19 according to an example embodiment.

In further embodiments, the base member 12 includes a first support pin aperture 27, shown in FIG. 20, and a second support pin aperture 29, shown in FIG. 19. The first support pin aperture 27 and second support pin aperture 29 may be individually configured to receive a support pin 17 (e.g. in a press fit or other manner of retention). The support pin 17 may extend into the central cavity 36 and may support the control shaft 16 such that the control shaft 16 will not bottom out against the top surface 32 of the base member 12.

In further embodiments, the base member 12 may include a first front guide groove 52, a second front guide groove 53, a first rear guide groove 54, and a second rear guide groove 55. The first front guide groove 52, second front guide groove 53, first rear guide groove 54, and second rear guide groove 55 may be utilized to customize the expansion profile of the implant 10, as will be discussed in further detail.

Figure 11:
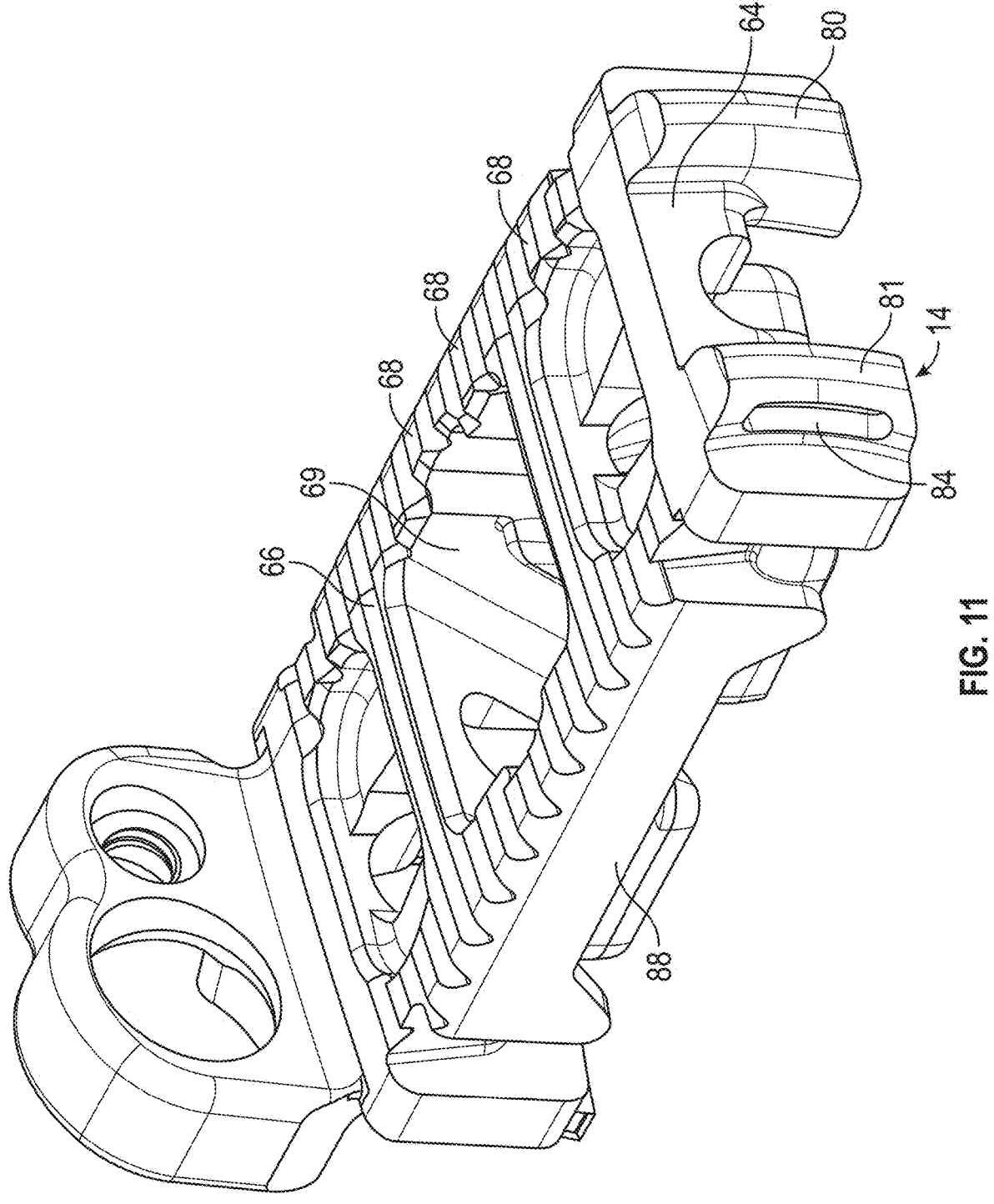
FIG. 11 is another perspective view of the adjustable member of FIG. 10 according to an example embodiment.
Figure 12:
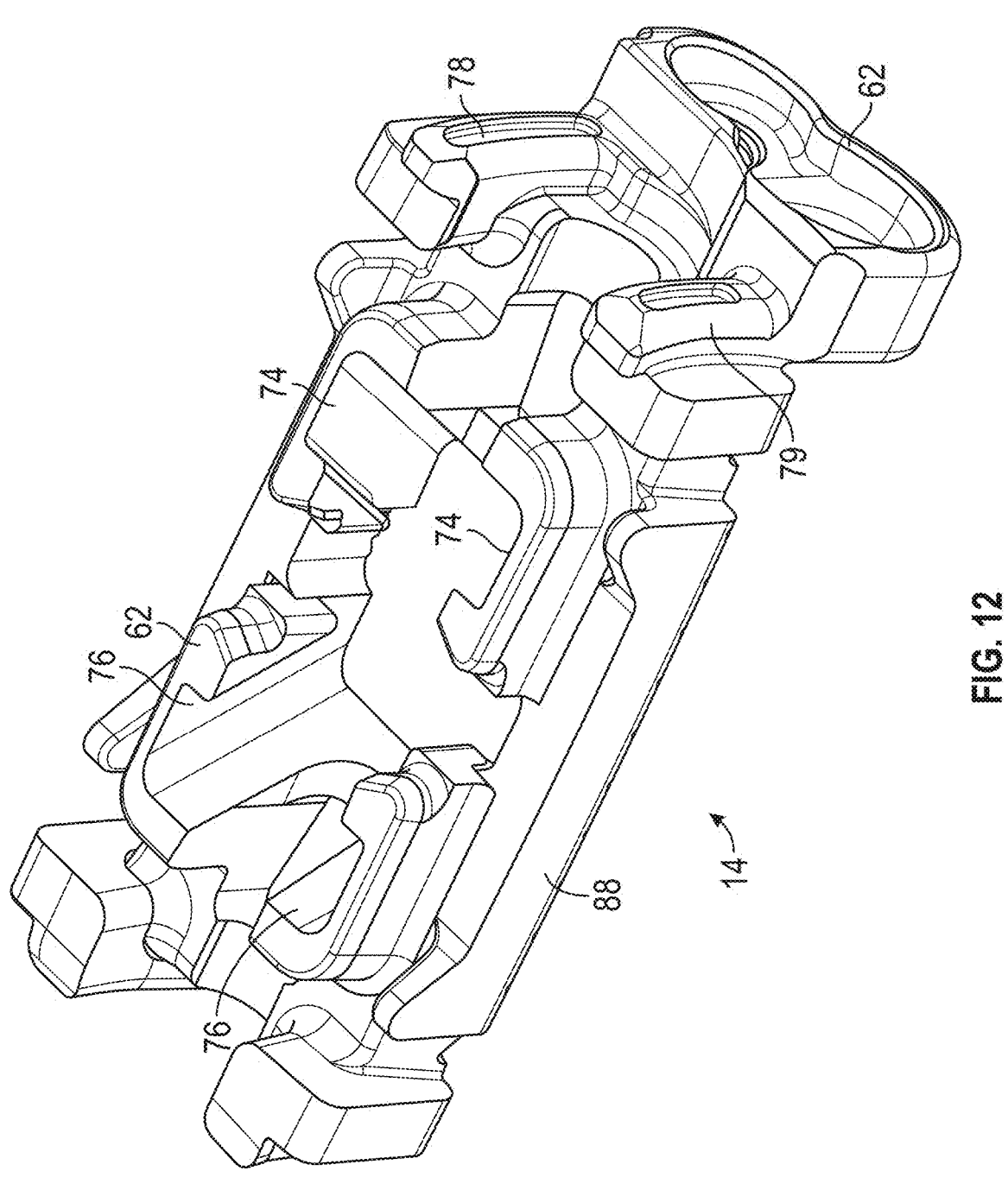
FIG. 12 is a perspective view of the underside of the adjustable member of FIG. 10 according to an example embodiment.
Figure 13:
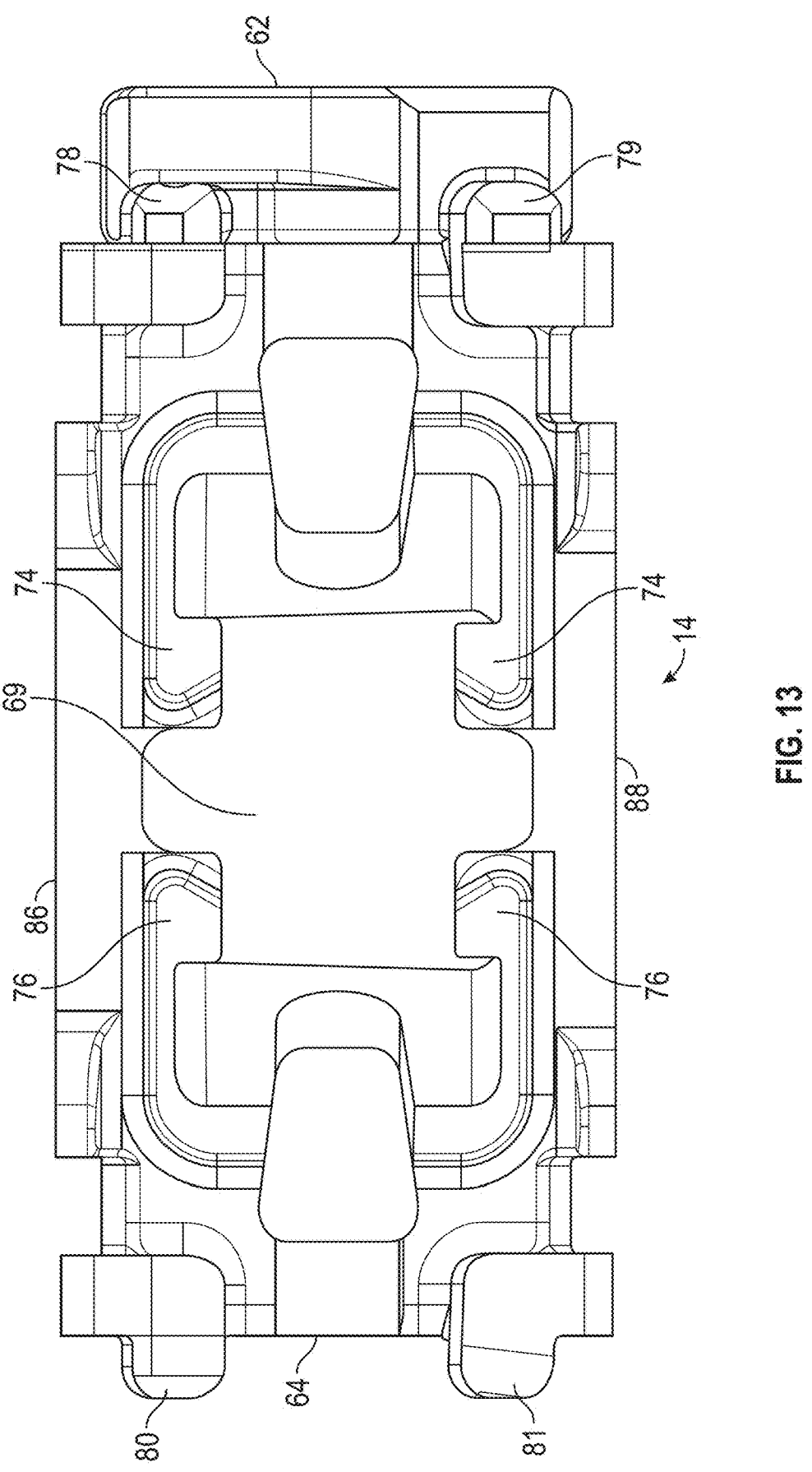
FIG. 13 is a bottom view of the adjustable member of FIG. 10 according to an example embodiment.

In some embodiments, as shown in FIGS. 11 and 12, the adjustable member 14 includes a front or first end 62, a rear or second end 64, and a central recess or cavity 69 positioned between the first end 62 and the second end 64. The adjustable member 14 further includes a top surface 66 having ridges or projections 68 formed by corresponding grooves and a bottom surface 67. The adjustable member 14 also includes a first side portion 86, and a second side portion 88. In some embodiments, the first and second side portions 86, 88 have a shape generally corresponding to the shape of the first side 38 and the second side 40 of the base member 12. In other embodiments, the first and second side portions 86, 88 have shapes differing from the shapes of the first side 38 and second side 40 of the base member 12.

Figure 5:
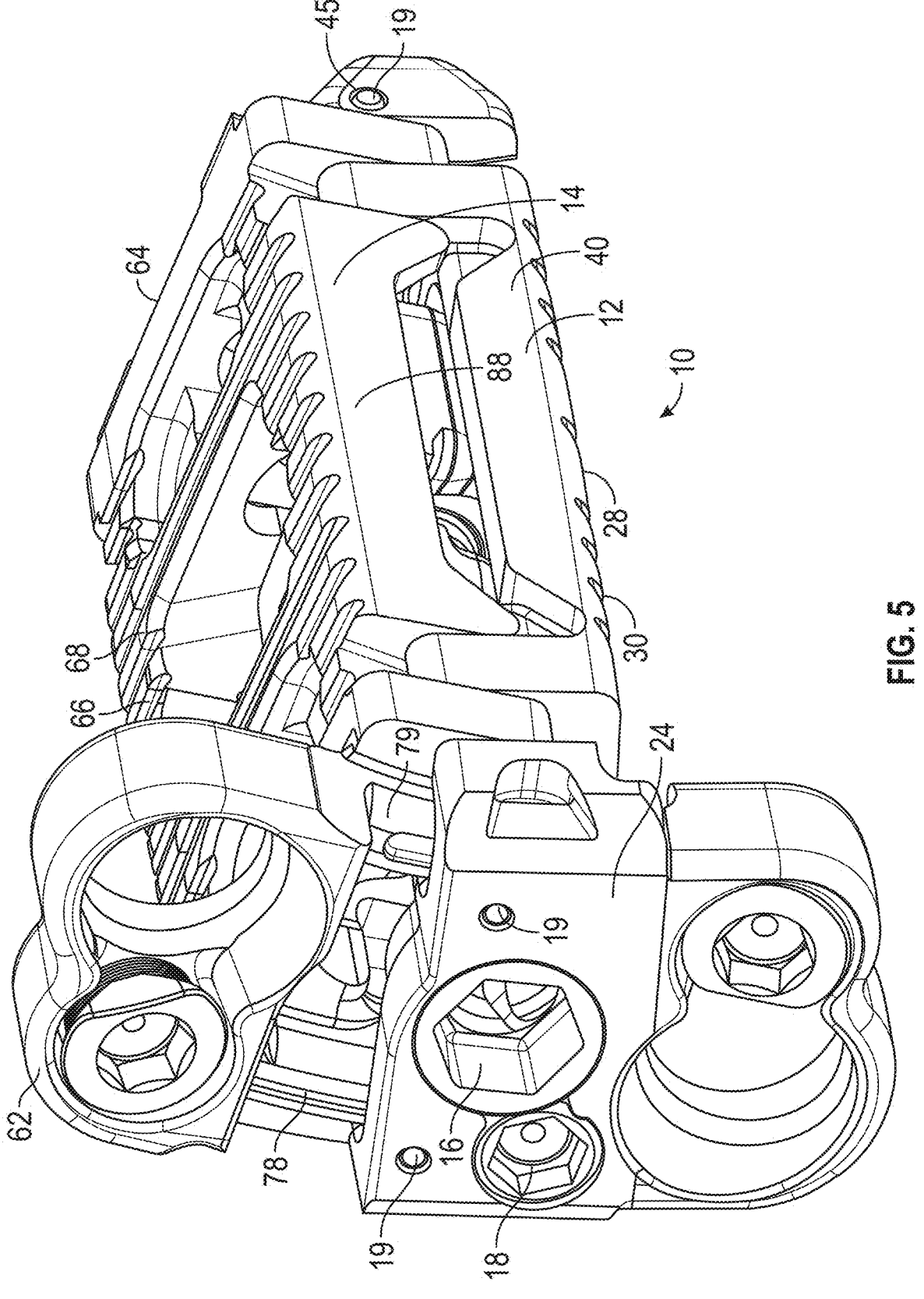
FIG. 5 is a perspective view of the implant of FIG. 1 in an expanded position according to an example embodiment.
Figure 6:
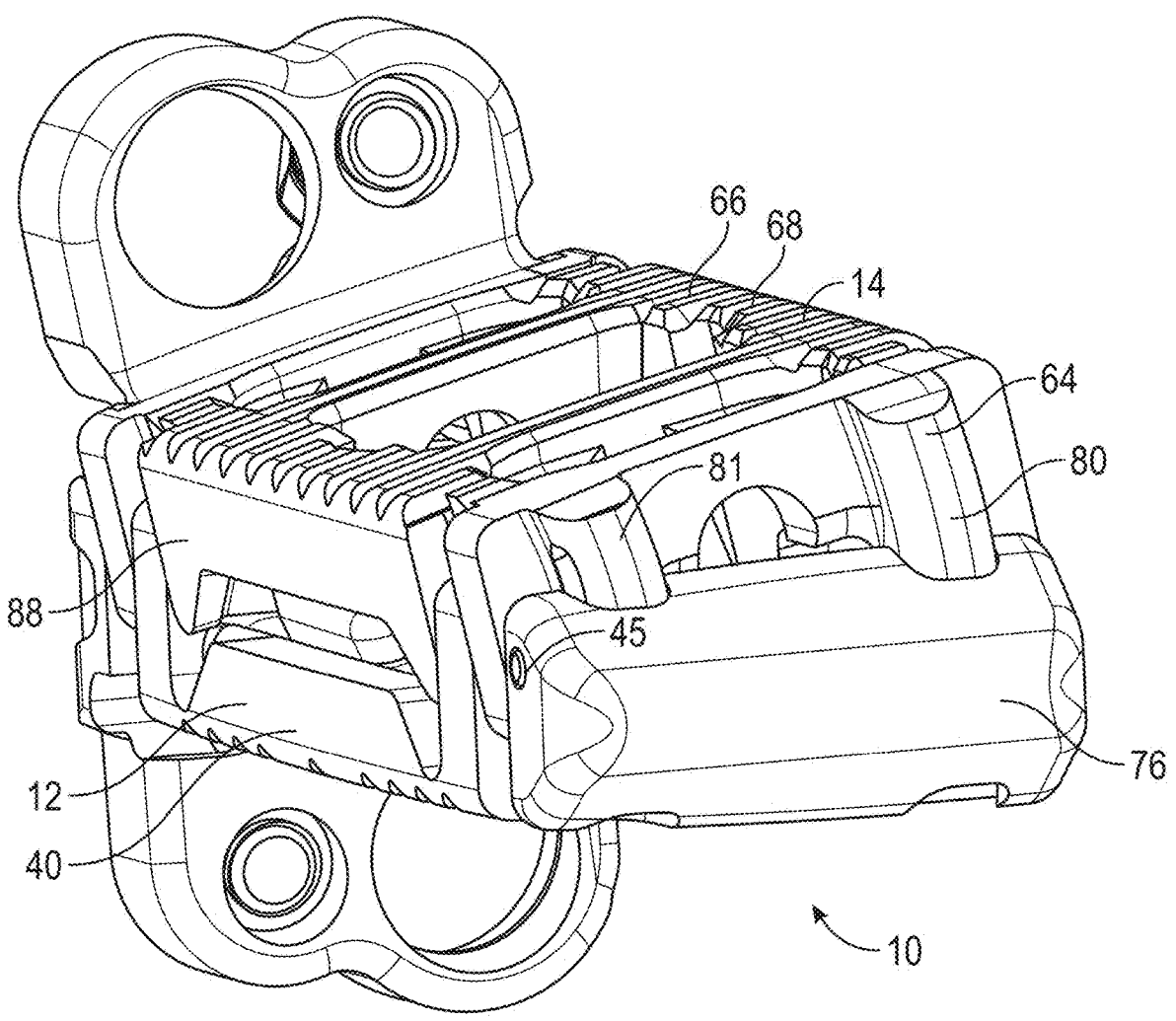
FIG. 6 is another perspective view of the implant of FIG. 1 in an expanded position according to an example embodiment.

As shown in FIG. 5, in further embodiments, the adjustable member 14 may include a first front guide rail 78, a second front guide rail 79, a first rear guide rail 80, and a second rear guide rail 81. In some embodiments, the first front guide rail 78 is configured to be received by the first front guide groove 52, the second front guide rail 79 is configured to be received by the second front guide groove 53, the first rear guide rail 80 is configured to be received by the first rear guide groove 54, and the second rear guide rail 81 is configured to be received by the second rear guide groove 55. According to an example embodiment, when the implant 10 expands (e.g. the adjustable member 14 moves in a direction away from the base member 12), the guide rails 78, 79, 80, 81 will individually translate within each respective guide groove 52, 53, 54, 55.

Figure 10:
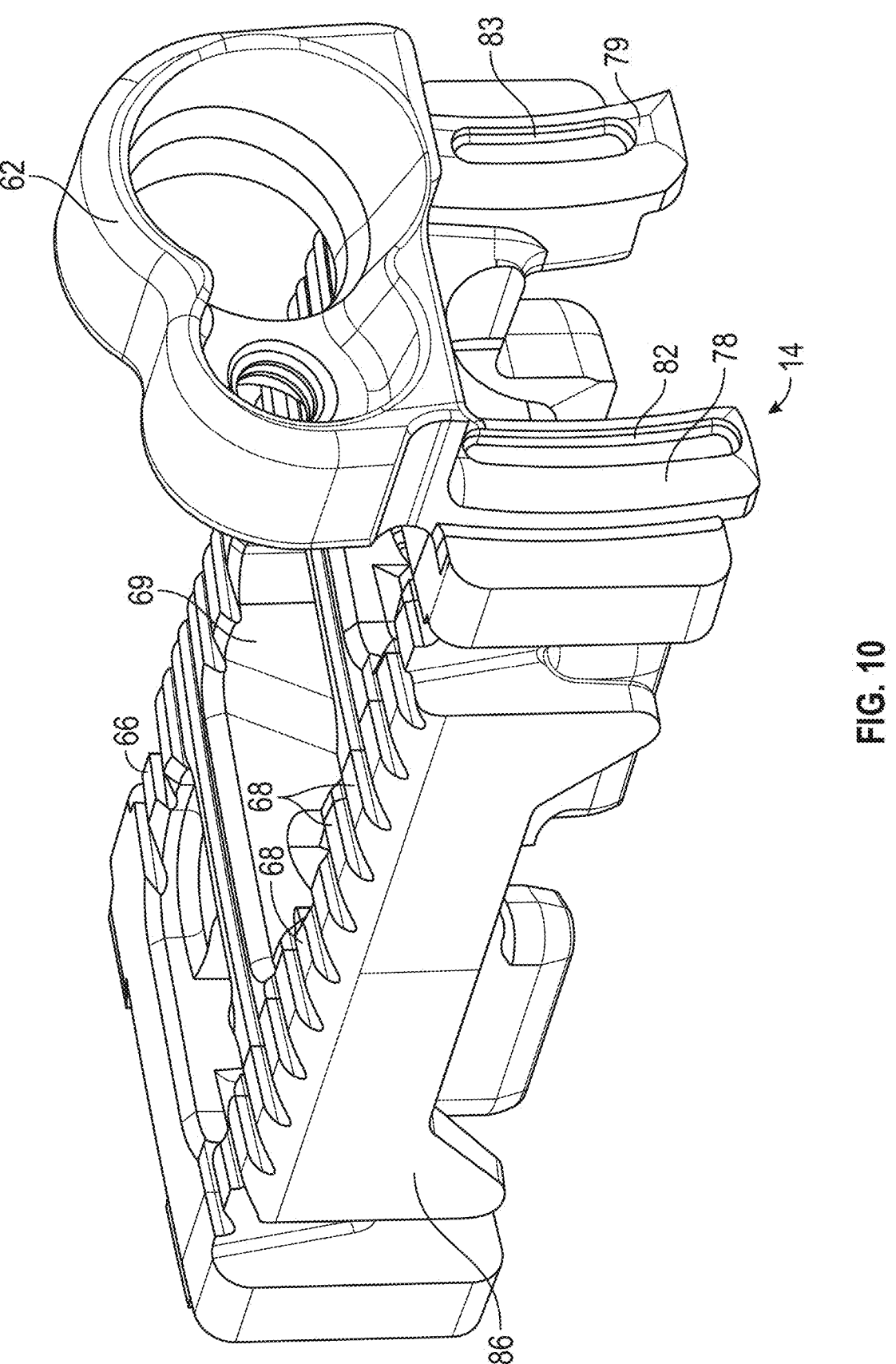
FIG. 10 is a perspective view of an adjustable member of the implant of FIG. 1 according to an example embodiment.

In further embodiments, such as the embodiment shown in FIG. 10, the first front guide rail 78 may include a first pin slot 82 configured to receive a retention pin 19. Further, the second front guide rail 79 may include a second pin slot 83 configured to receive a retention pin 19. Further, the first rear guide rail 80 may include a third pin slot configured to receive a retention pin 19. In some embodiments, such as the embodiment shown in FIG. 1, the first guide rail 80 does not include a third pin slot. Further, the second rear guide rail 81 may include a fourth pin slot 84 configured to receive a retention pin 19.

Referring to FIGS. 10-13, in some embodiments, the adjustable member 14 includes one or more control channels, such as a first control channel 74 and a second control channel 76. The first control channel 74 receives the first control member 20, and the second control channel 76 receives the second control member 22. In some embodiments, the control members 20, 22 are received in the control channels 74, 76 in a sliding manner such that the control members 20, 22 are able to translate within the control channels 74, 76. In further embodiments, each control channel has a shape such that the control channel surrounds the control member and at least partially corresponds in shape to the control member.

Figure 14:
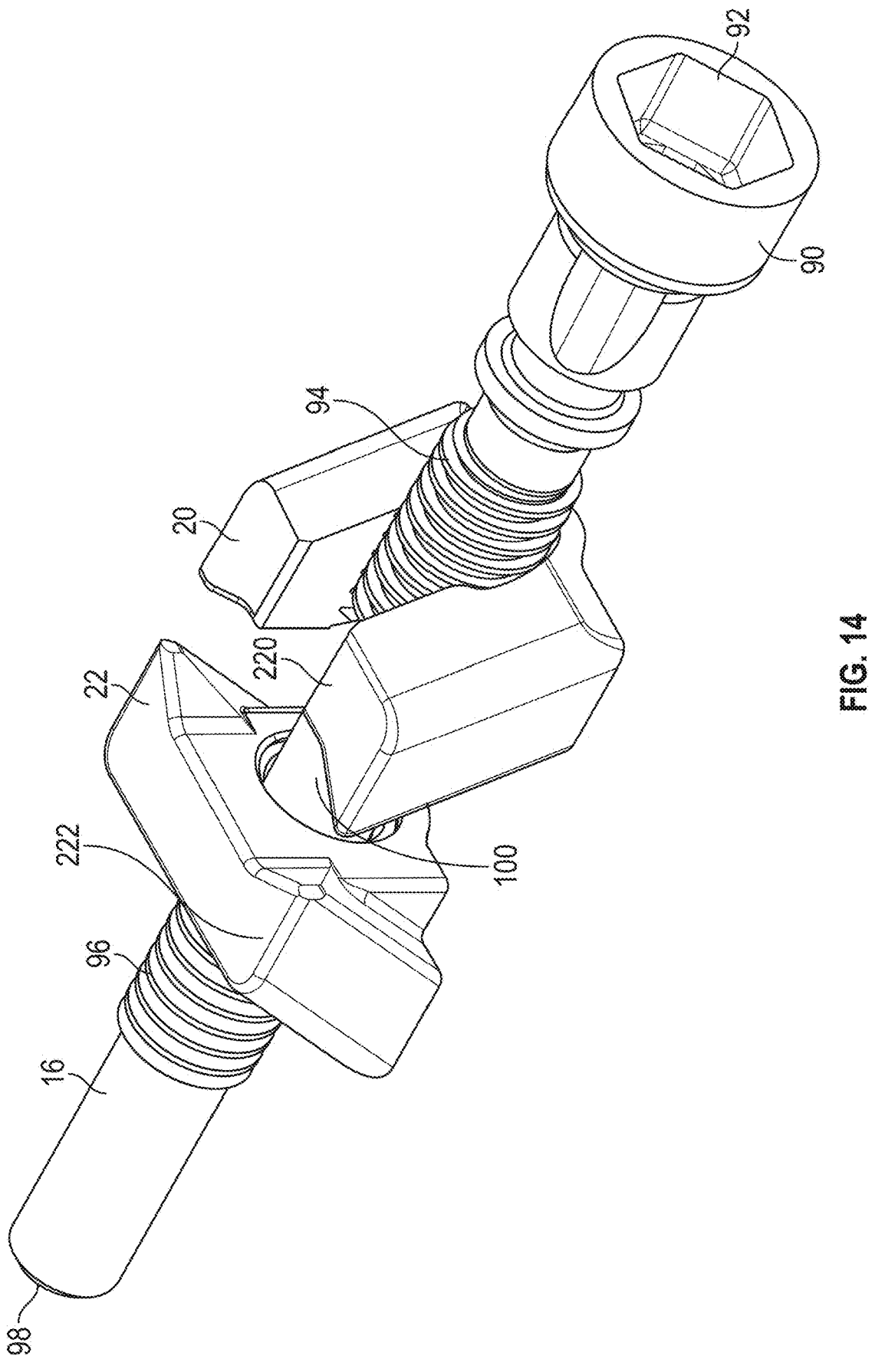
FIG. 14 is a perspective view of a control shaft and two control members of the implant of FIG. 1 according to an example embodiment.
Figure 15:
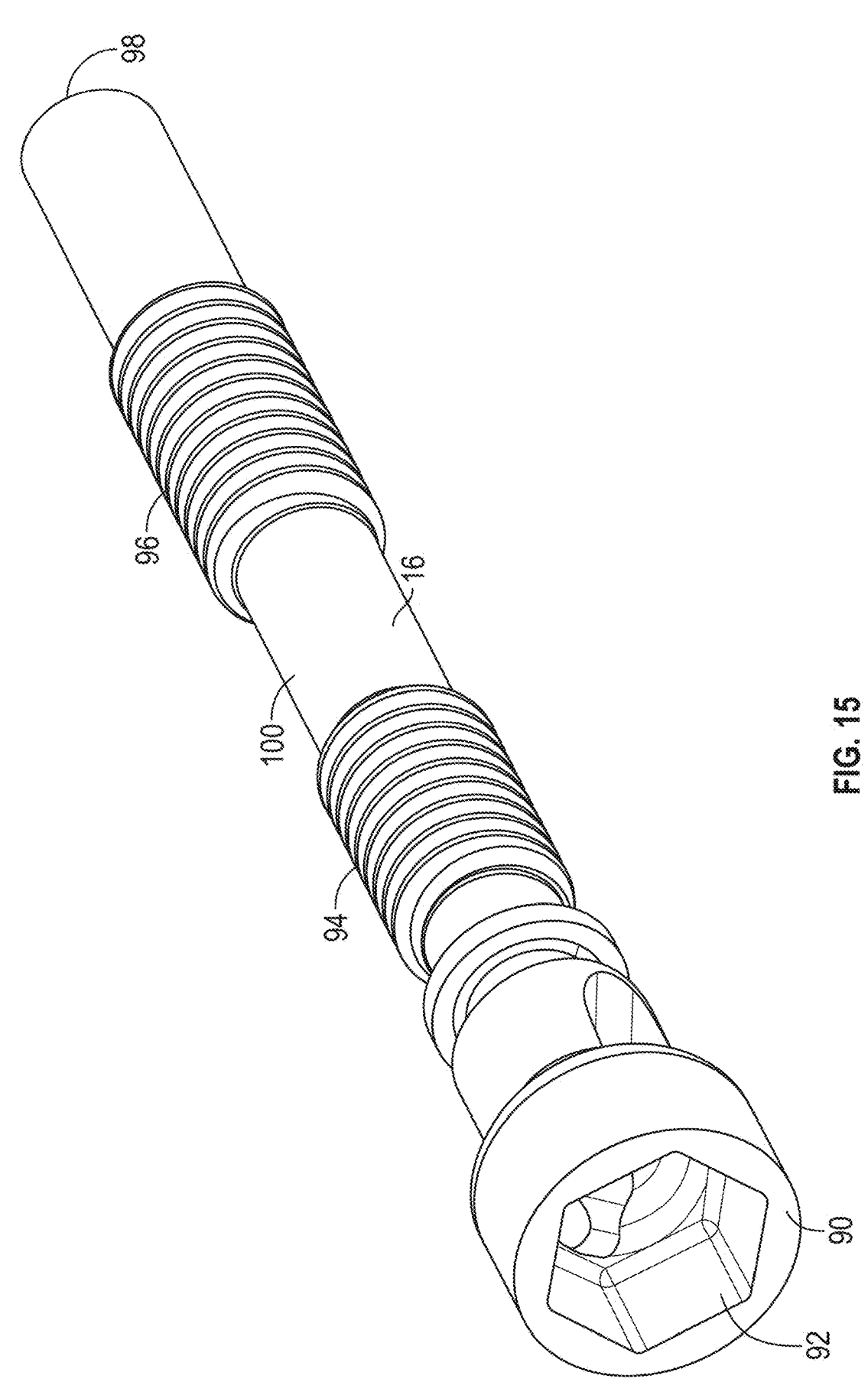
FIG. 15 is a perspective view of the control shaft of FIG. 14 according to an example embodiment.

Referring to FIGS. 14 and 15, the control shaft 16 includes a head portion 90, a tool port 92 disposed within the head portion 90, and a tip 98 located at an end opposite the head portion 90. In some embodiments, the tip 98 is flat, while in other embodiments, the tip 98 may be pointed or beveled. In some embodiments, the control shaft 16 further includes a first control thread 94 and a second control thread 96. A non-threaded portion 100 may be located between the first control thread 94 and the second control thread 96.

Figure 16:
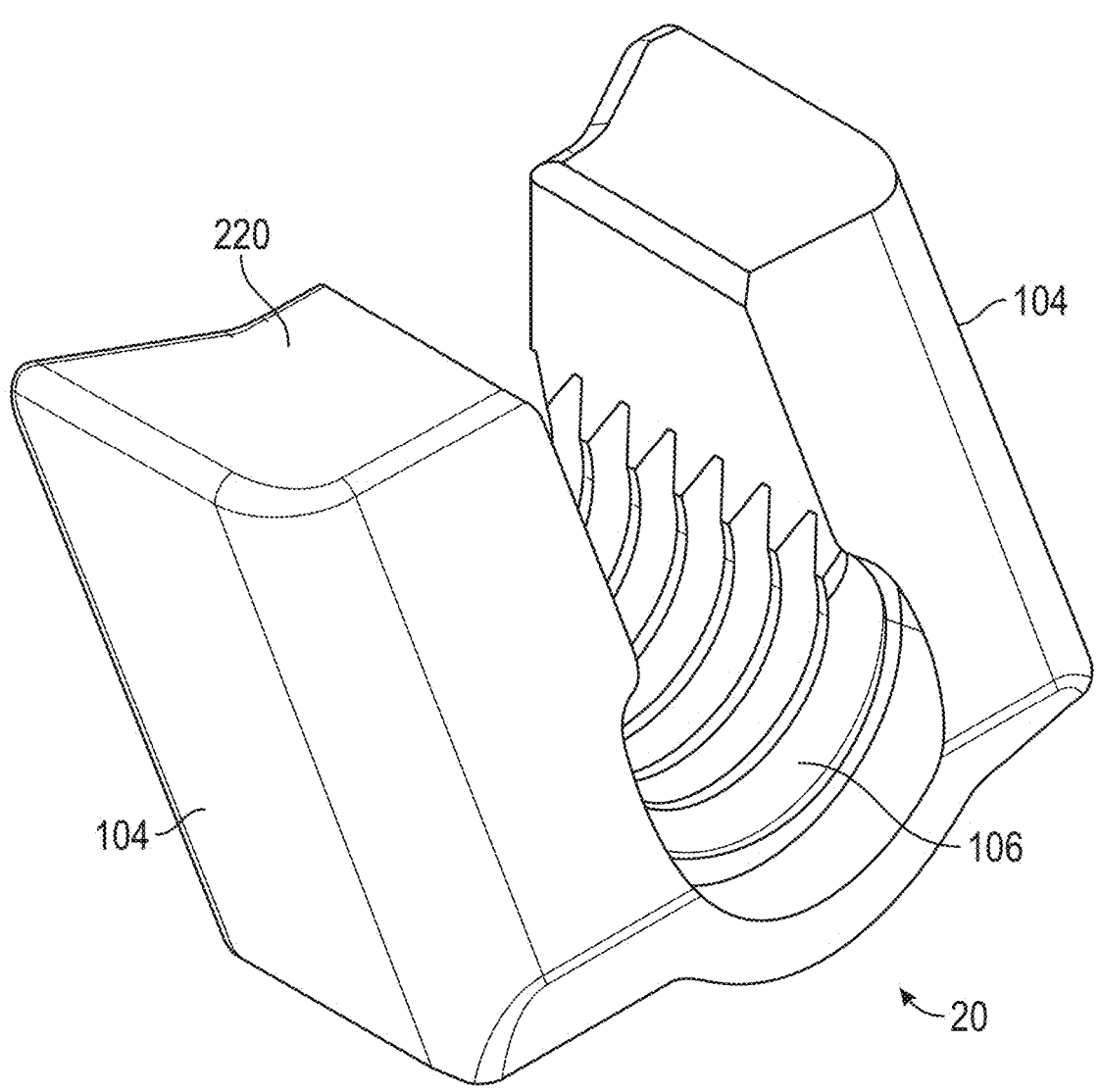
FIG. 16 is a perspective view of a control member of the implant of FIG. 1 according to an example embodiment.

As shown in FIG. 16, the first control member 20 includes a top portion 220, one or more flat portions 104, and an internal thread 106. In some example embodiments, the first control member 20 is configured to be received by the first control channel 74, such that the flat portions 104 engage with the walls of the first control channel 74.

Figure 17:
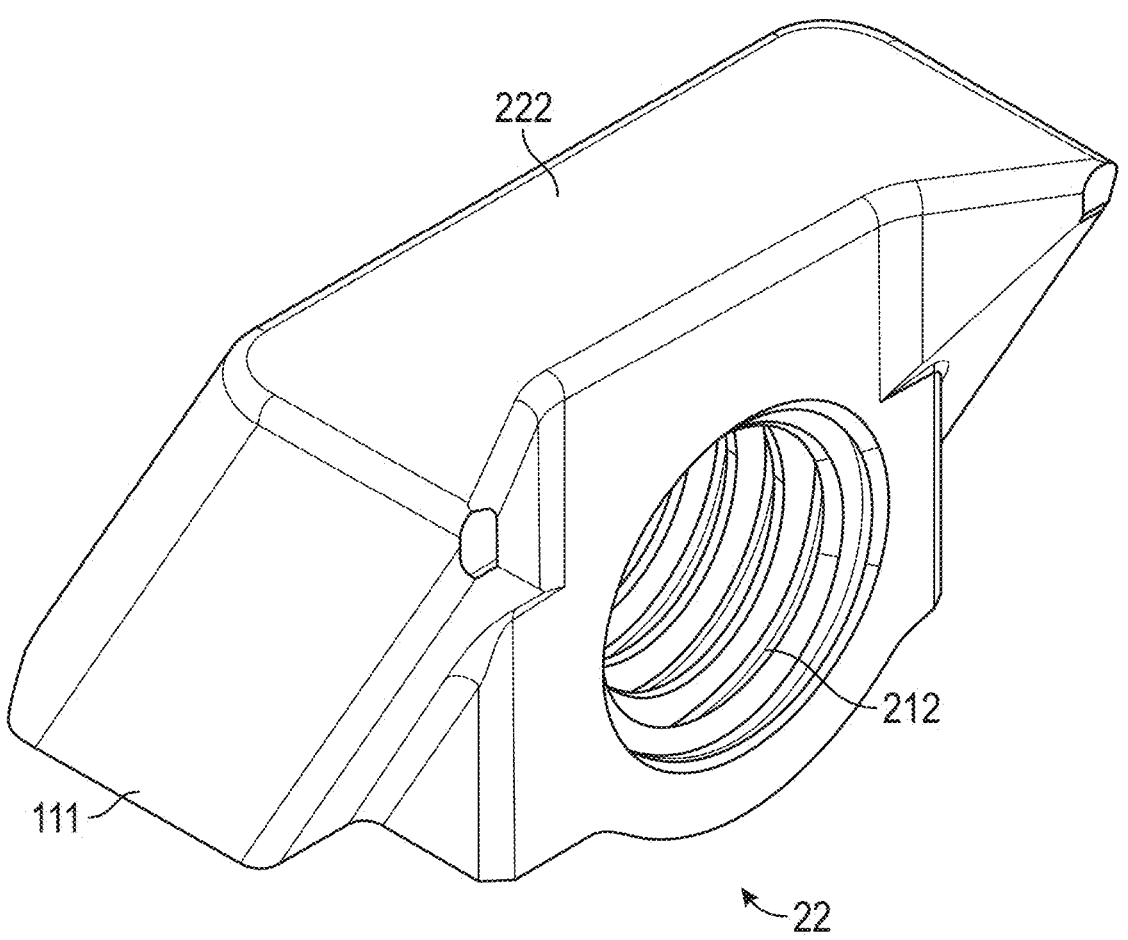
FIG. 17 is a perspective view of a control member of the implant of FIG. 1 according to an example embodiment.

As shown in FIG. 17, the second control member 22 includes a top portion 220, one or more flat portions 111, and an internal thread 212. In some example embodiments, the second control member 22 is configured to be received by the second control channel 76, such that the flat portions 111 engage with the walls of the second control channel 76. In some example embodiments, the first control member 20 and the second control member 22 move or translate along the control shaft 16 and within or on the first control channel 74 and the second control channel 76, as will be described further herein.

Referring back to FIGS. 1-8, in some embodiments, the implant 10 is movable between at least a first, collapsed position, as shown in FIGS. 1-4, and a second, expanded position, shown in FIGS. 5-8. In the first position, the control shaft 16 is received by the control bore 48 and positioned within the central cavity 36 of the base member 12. In some embodiments, the first side 38 and the second side 40 of the base member 12 receive the first side 86 and the second side 88 of the adjustable member when the implant 10 is in the collapsed position, such that the projections and recesses have a relatively close fit to enable proper alignment between the adjustable member 14 and the base member 12, as shown in FIGS. 1-4. In other embodiments, the projections and recesses have a relatively loose fit to enable a desired angular offset between the adjustable member 14 and the base member 12.

In some embodiments, the control shaft 16 is received by the base member 12 such that the head 90 is positioned within the control bore 48 (see FIG. 9), the first control thread 94 and the second control thread 96 are positioned within the central cavity 36, and the head portion 90 is positioned within the tip bore 50 of the second end 26 of the base member 12. In some embodiments, the control shaft 16 is rotatable within the base member 12. The first control member 20 is received on the first control thread 94 of the control shaft 16, and the second control member 22 is received on the second control thread 96 of the control shaft 16.

In some embodiments, such as the embodiment shown in FIG. 14, the first control thread 94 and the second control thread 96 are threaded in opposite manners (e.g., left-handed and right-handed), such that upon rotation of the control shaft 16, the control members 20, 22 move in opposite directions along the control shaft 16. For example, the control shaft 16 may be configured such that rotation of the control shaft 16 in a first direction (e.g., clockwise) causes the first and second control members 20, 22 to move toward each other, and rotation of the control shaft 16 in a second direction (e.g., counter-clockwise) causes the first and second control member 20, 22 to move away from each other.

As the control members 20, 22 move along the control shaft 16, the control members 20, 22 further move within the control channels 74, 76, thereby causing relative movement of the adjustable member 14 and the base member 12. As the control members 20, 22 translate along the control shaft 16, the adjustable member 14 is moved upward or downward due to the angled shape of the first and second control channels 74, 76. Assuming a constant turn rate of the control shaft 16, the rate of movement of the control members 20, 22, and therefore the adjustable member 14, can be adjusted by modifying the slope of the control channels 74, 76 relative to the control shaft 16.

Figure 27A:
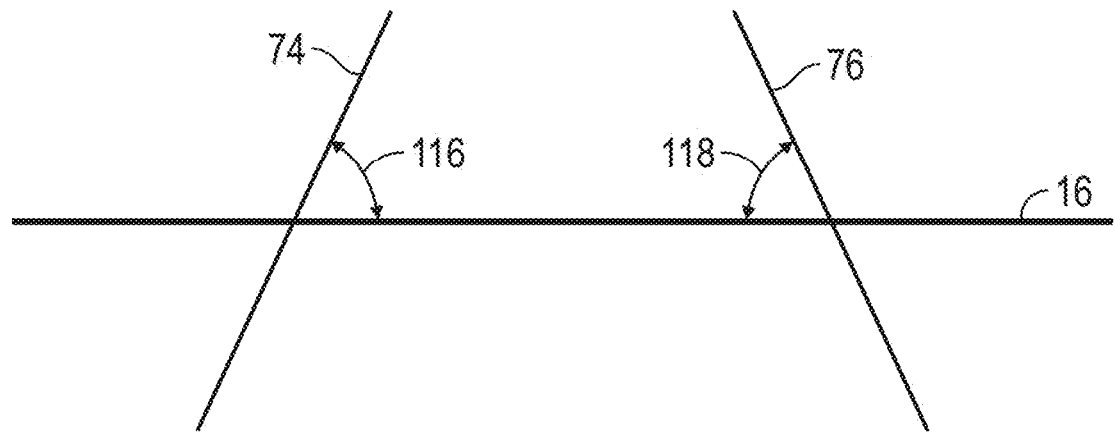
FIGS. 27A-B are schematic representations of a control mechanism according to an example embodiment.
Figure 27B:
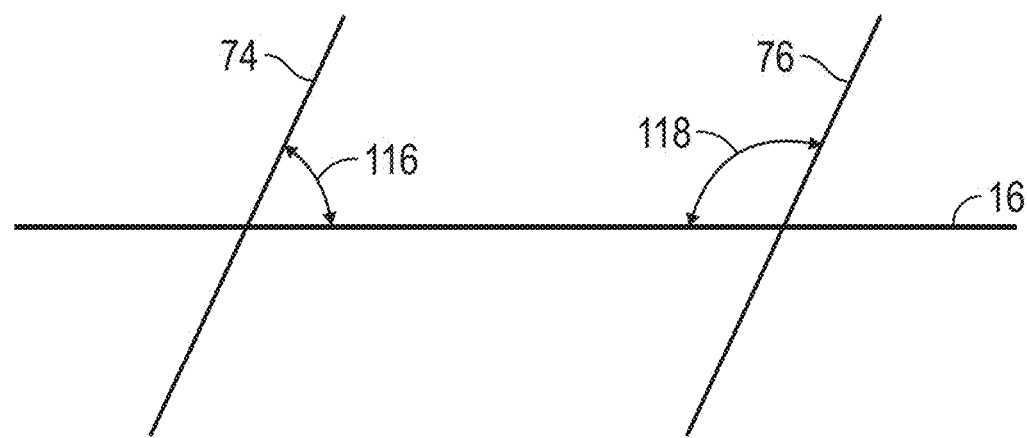

For example, referring to FIGS. 27A-C, schematic representations of the control shaft 16, the first control channel 74, and the second control channel 76 are shown according to various alternative embodiments. The first control channel 74 extends at a first angle 116 relative to the control shaft 16, and the second control channel 76 extends at a second angle 118 relative to the control shaft 16. The first and second angles 116, 118 define the rate at which the first control member 20 and the second control member 22 cause corresponding movement (e.g., expansion) of the first and second ends 62, 64 of the adjustable member 14 relative to the base member 12. As shown in FIG. 27A, in some embodiments, the first angle 116 and second angle 118 are approximately the same, and the control channels 74, 76 define linear paths, such that the rates of movement of the first and second ends 62, 64 of the adjustable member 14 are substantially the same and constant (assuming a constant rate of rotation of the control shaft 16). As shown in FIG. 27B, in some embodiments, rather than being angled toward each other in an upward direction, the first and second control channels 74, 76 may extend in a parallel manner or be configured to extend upward at angles in the same general direction.

Providing differing configurations for the first control channel 74 and the second control channel 76 enables customization of the characteristics of the implant 10 in the second, expanded position. For example, the control channels 74, 76 may be configured such that in a fully expanded position of the implant 10, one of the first end 62 and the second end 64 of the adjustable member 14 is expanded to a greater degree than the opposing end. Other configurations of the first and second control channels 74, 76 are possible according to various alternative embodiments.

In further embodiments, characteristics of the implant 10 in the second, expanded position may be further customized using at least one guide rail. For example, the implant 10 according to the example embodiment shown in FIGS. 5-8 has an angular expansion profile, wherein the top surface 66 of the adjustable member 14 and the bottom surface 28 of the base member 12 are not substantially parallel, but instead form an angle. The angle that the top surface 66 of the adjustable member 14 and the bottom surface 28 of the base member 12 form when the implant 10 is in the expanded position may be customized based on patient needs. For example, when the implant 10 is installed into a patient's spine, the angle that the top surface 66 of the adjustable member 14 and the bottom surface 28 of the base member 12 form when the implant 10 is in the expanded position may vary depending on the curvature of the patient's spine at the location the implant 10 is installed.

According to an example embodiment, an angular expansion profile of the implant 10 may be achieved using at least one guide rail and at least one control member. For example, in the example embodiment shown in FIGS. 5-8, the control shaft 16 is received by the base member 12 such that the head 90 is positioned within the control bore 48, the first control thread 94 and the second control thread 96 are positioned within the central cavity 36, and the end portion 98 is positioned within the tip bore 50 of the second end 26 of the base member 12 (see FIG. 7). In this embodiment, the control shaft 16 is rotatable within the base member 12. The first control member 20 is received on the first control thread 94 of the control shaft 16, and the second control member 22 is received on the second control thread 96 of the control shaft 16.

In this example embodiment, the first control thread 94 and the second control thread 96 are threaded in opposite manners (e.g., left-handed and right-handed), such that upon rotation of the control shaft 16, the control members 20, 22 move in opposite directions along the control shaft 16. In this example embodiment, the control shaft 16 is configured such that rotation of the control shaft 16 in a first direction (e.g., clockwise) causes the first and second control members 20, 22 to move toward each other, and rotation of the control shaft 16 in a second direction (e.g., counter-clockwise) causes the first and second control member 20, 22 to move away from each other.

As the control members 20, 22 move along the control shaft 16, the control members 20, 22 further move within the control channels 74, 76, thereby causing relative movement of the adjustable member 14 and the base member 12. As the control members 20, 22 translate along the control shaft 16, the adjustable member 14 is moved upward or downward due to the angled shape of the first and second control channels 74, 76. The rate of movement of the control members 20, 22 and the adjustable member 14 can therefore be adjusted by modifying the slope of the control channels 74, 76 relative to the control shaft 16.

When the control shaft 16 is turned in a second direction (e.g. counter-clockwise), the control members 20, 22 translate along the control shaft 16 away from each other. In doing so, the control members 20, 22 also translate within the control channels 74, 76 causing the adjustable member 14 to generally move away from the base member 12. Further, when the adjustable member 14 moves away from the base member 12, the guide rails 78, 79, 80, 81 individually translate within each respective guide groove 52, 53, 54, 55. In some embodiments, the guide rails 78, 79, 80, 81 and the guide grooves 52, 53, 54, 55 may run perpendicular to the top surface 66 of the adjustable member 14, thereby causing the adjustable member 14 to move upwards in a linear manner. In these example embodiments, the top surface 66 of the adjustable member 14 will be substantially parallel to the bottom surface 28 of the base member 12 when the implant 10 is in a second, expanded position. In other embodiments, such as the embodiments shown in FIGS. 5-8, the guide rails 78, 79, 80, 81 and the guide grooves 52, 53, 54, 55 may have a curvature. The curvature of the guide rails 78, 79, 80, 81 and the guide grooves 52, 53, 54, 55 will cause the adjustable member 14 to move upwards in a non-linear manner. Therefore, the implant 10 will have an angular expansion profile (e.g. the top surface 66 of the adjustable member 14 and the bottom surface 28 of the base member 12 are not substantially parallel, but instead form an angle).

In some embodiments, the first front guide rail 78 may have a larger radius (e.g. the radius of the circular arc which best approximates the curve of the guide rail at that point) than the second front guide rail 78 and the first rear guide rail 80 may have a larger radius (e.g. the radius of the circular arc which best approximates the curve of the guide rail at that point) than the second rear guide rail 81.

In further embodiments, the guide rails may include a linear portion and a curved portion allowing the implant 10 to expand linearly and angularly while expanding from the collapsed position to the expanded position. The expansion profile of the implant 10 may be further customized by altering the shape of the guide rails and guide grooves as needed.

In further embodiments, the guide rails may be linear. In this embodiment, an angular expansion profile may be accomplished by altering the lengths of the pin slots 82, 83, 84. As discussed in further detail below, when a pin 19 is inserted into a pin aperture 42, 43, 45 and into a pin slot 82, 83, 84, the pin 19 may bottom out against the bottom of the pin slot 82, 83, 84, thereby preventing the implant 10 from over expanding. As shown in FIG. 10, in some embodiments, the first pin slot 82 is longer than the second pin slot 83. Therefore, when the pins 19 are bottomed out against the bottom of the pin slots 82, 83, such as the embodiment shown in FIG. 5, the first lateral side portion 86 will be expanded a greater distance than the second lateral side portion 88. Therefore, an implant may include a linear guide rail on a first lateral side having a pin slot and a linear guide rail on a second lateral side. In this embodiment, if the pin slot on the first lateral side is longer than the pin slot on the second lateral side, the first lateral side will be able to expand a further distance than the second lateral side before the pins bottom out in the pin slots, thereby creating an angular expansion profile.

In this example embodiment, the angular expansion profile may be customized based on how many radians the control shaft 16 is turned in the second direction (e.g. counter-clockwise). As the control shaft 16 is turned in the second direction (e.g. counter-clockwise), the magnitude of the angle that the top surface 66 of the adjustable member 14 and the bottom surface 28 of the base member 12 will increase. Therefore, according to this example embodiment, there is a direct relationship between the number of radians the control shaft 16 is turned in the second direction (e.g. counter-clockwise) and the magnitude of the angle between the top surface 66 of the adjustable member 14 and the bottom surface 28 of the base member 12 of the implant 10 when the implant 10 is in a second, expanded position.

The magnitude of the angle that the top surface 66 of the adjustable member 14 and the bottom surface 28 of the base member 12 may also be customized by changing the curvature of the guide rails 78, 79, 80, 81 and the curvature of the guide grooves 52, 53, 54, 55. For example, adjusting the radii (e.g. the radius of the circular arc which best approximates the curve of the guide groove at that point) of the guide grooves 52, 53, 54, 55 and the radii (e.g. the radius of the circular arc which best approximates the curve of the guide rail at that point) of the guide rails 78, 79, 80, 81 will cause a change in the angular expansion profile of the implant 10. For example, decreasing the radii (e.g. the radius of the circular arc which best approximates the curve of the guide groove at that point) of the guide grooves 52, 53, 54, 55 and the radii (e.g. the radius of the circular arc which best approximates the curve of the guide rail at that point) of the guide rails 78, 79, 80, 81 will result in a larger angle between the top surface 66 of the adjustable member 14 and the bottom surface 28 of the base member 12. Therefore, according to this example embodiment, there is an inverse relationship between magnitude of the radii of the guide rails 78, 79, 80, 81 and the magnitude of the angle between the top surface 66 of the adjustable member 14 and the bottom surface 28 of the base member 12 of the implant 10 when the implant 10 is in a second, expanded position.

Figure 3:
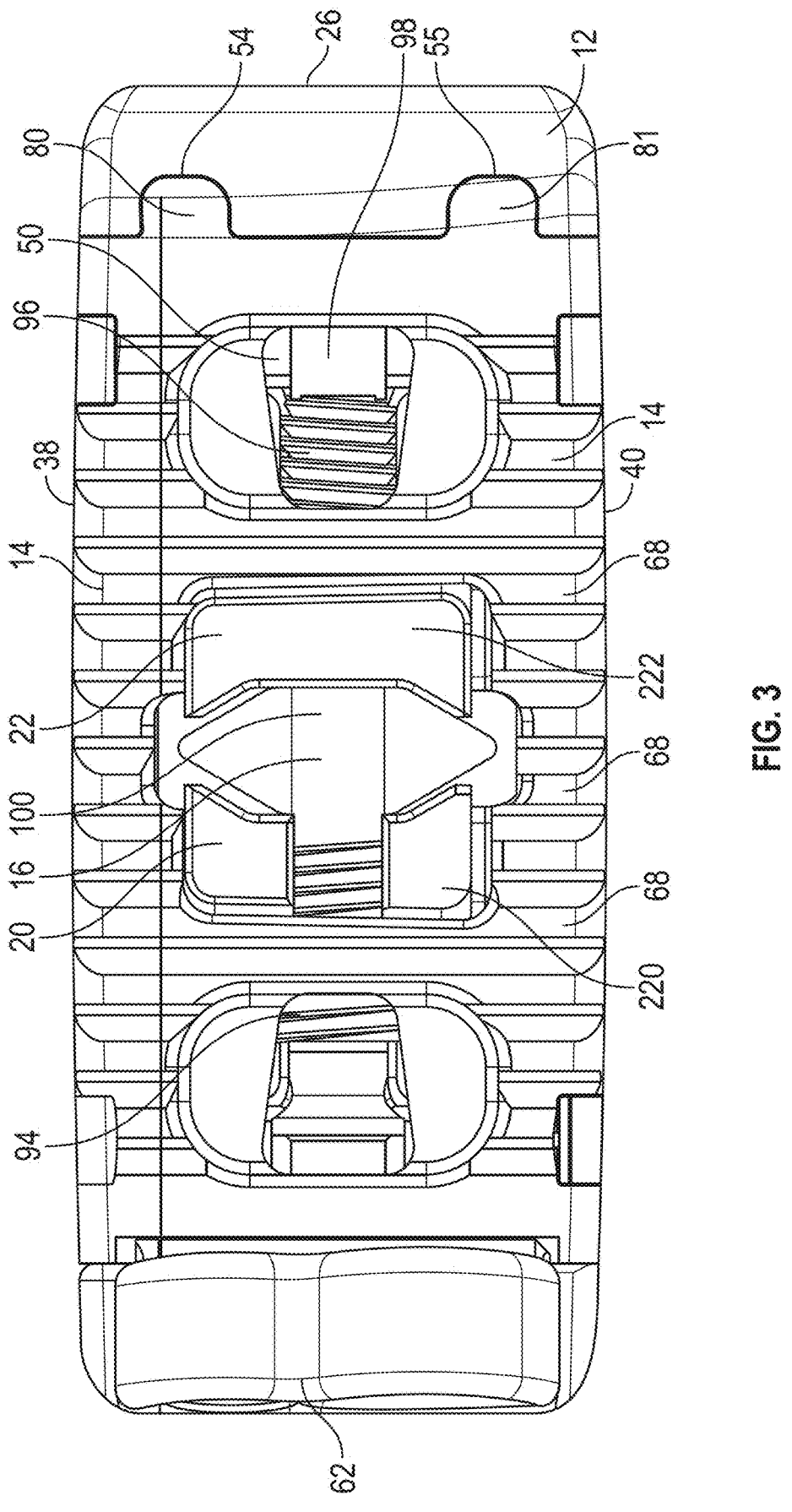
FIG. 3 is a top view of the implant of FIG. 1 in a collapsed position according to an example embodiment.
Figure 4:
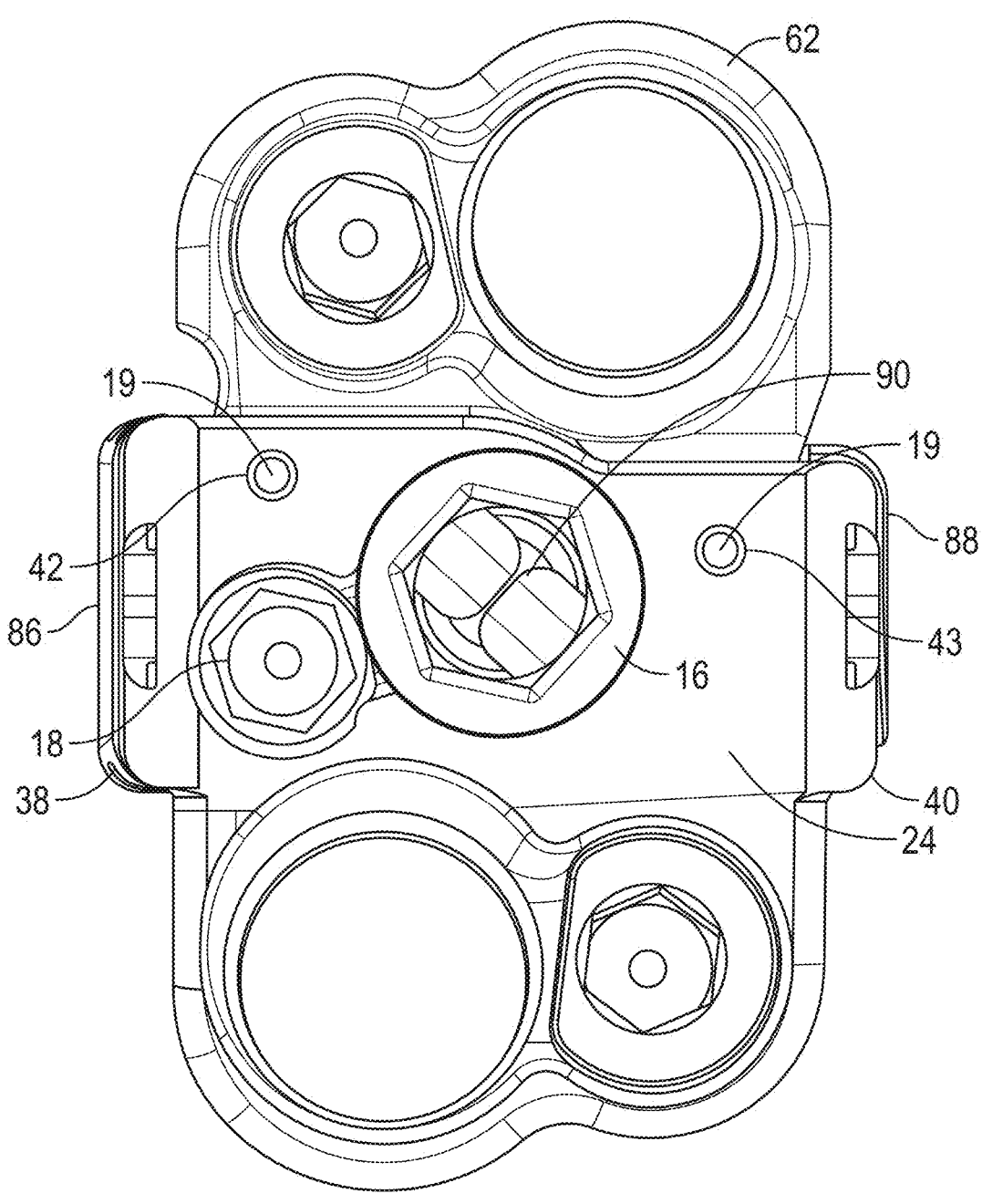
FIG. 4 is a front view of the implant of FIG. 1 in a collapsed position according to an example embodiment.
Figure 7:
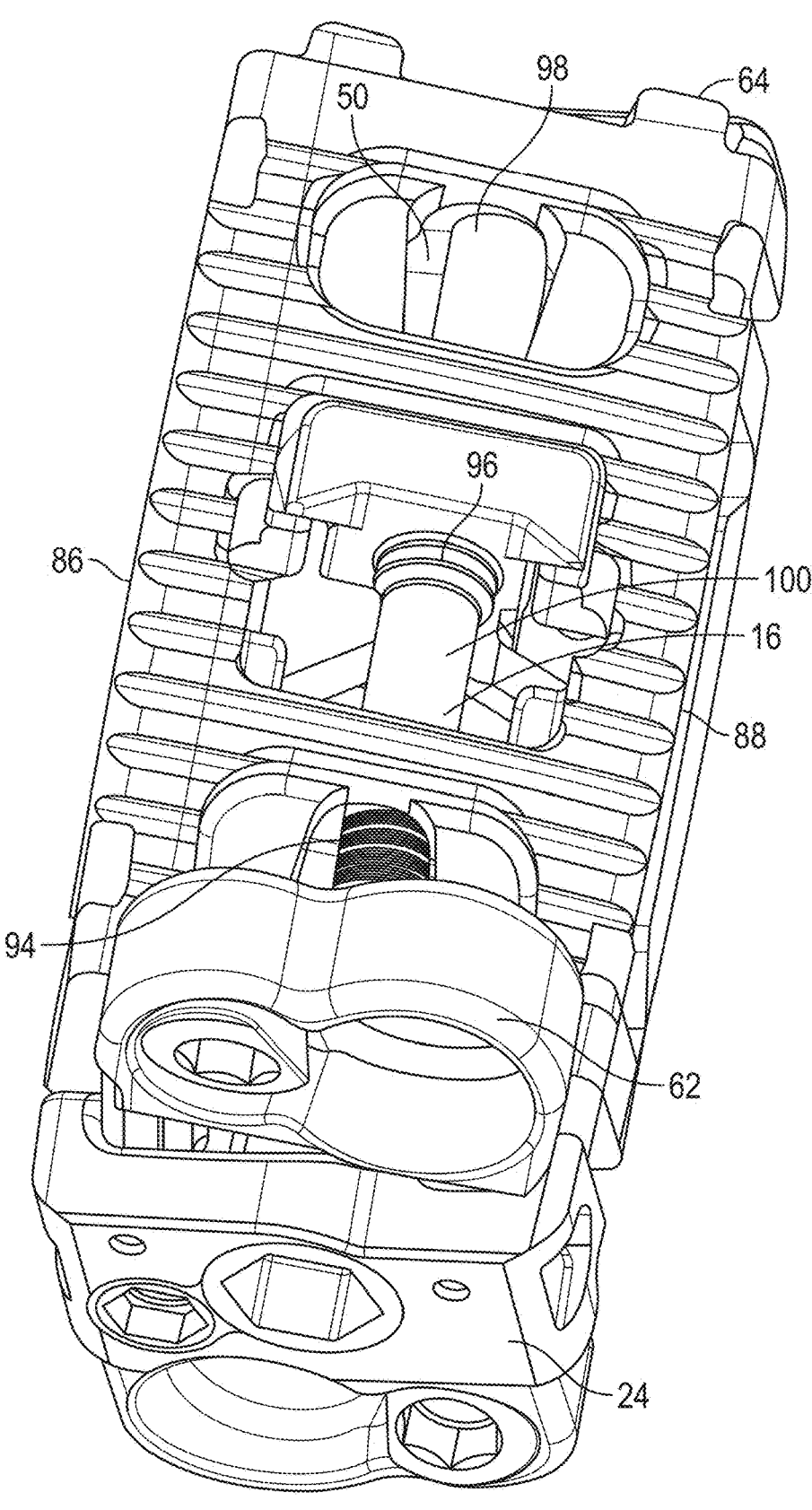
FIG. 7 is another perspective view of the implant of FIG. 1 in an expanded position according to an example embodiment.
Figure 8:
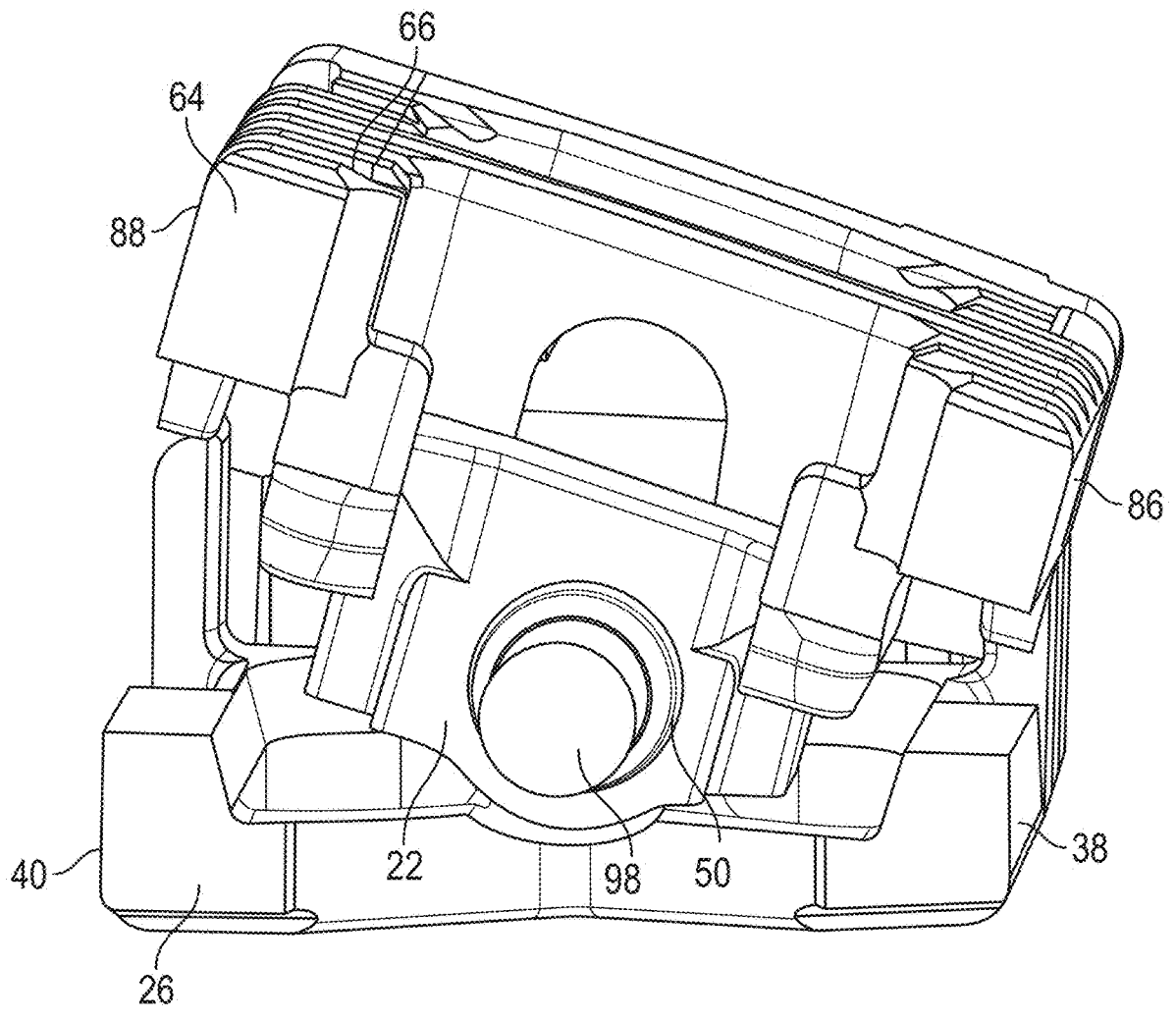
FIG. 8 is a rear view of the implant of FIG. 1 in an expanded position according to an example embodiment.

In an example embodiment, as the implant 10 expands in an angular fashion, as shown in FIGS. 5-8, the control shaft 16 will not necessarily be centered in the implant 10. For example, as shown in FIG. 3, the tip 98 is centered in the tip bore 50 when the implant 10 is in the collapsed position. However, as shown in FIG. 7, when the implant 10 is in the expanded position, the tip 98 of the control shaft 16 is no longer centered in the tip bore 50, but is instead offset.

In use, the implant 10 is positioned within a desired space (e.g., between adjacent portions of bone) while in the first, collapsed position, as shown in FIG. 1. To position the implant 10, an appropriate tool may be used to engage tool recesses 56 and to manipulate the implant 10 into a desired position. Once in a desired position, a subsequent tool may be utilized to engage the tool port 92 and to rotate the control shaft 16 to move the adjustable member 14 to a desired degree of expansion. It should be noted that based on a particular application, the adjustable member 14 may be utilized in a fully collapsed position, a fully expanded position, or any intermediate position therebetween. Once the implant 10 is properly positioned and expanded to a desired height, bone graft material may be inserted into the central cavity 36. The various apertures in and through the base member 12 and the adjustable member 14 may in some embodiments facilitate the growth of bone material in and around the implant 10 to further stabilize the device.

Figure 9:
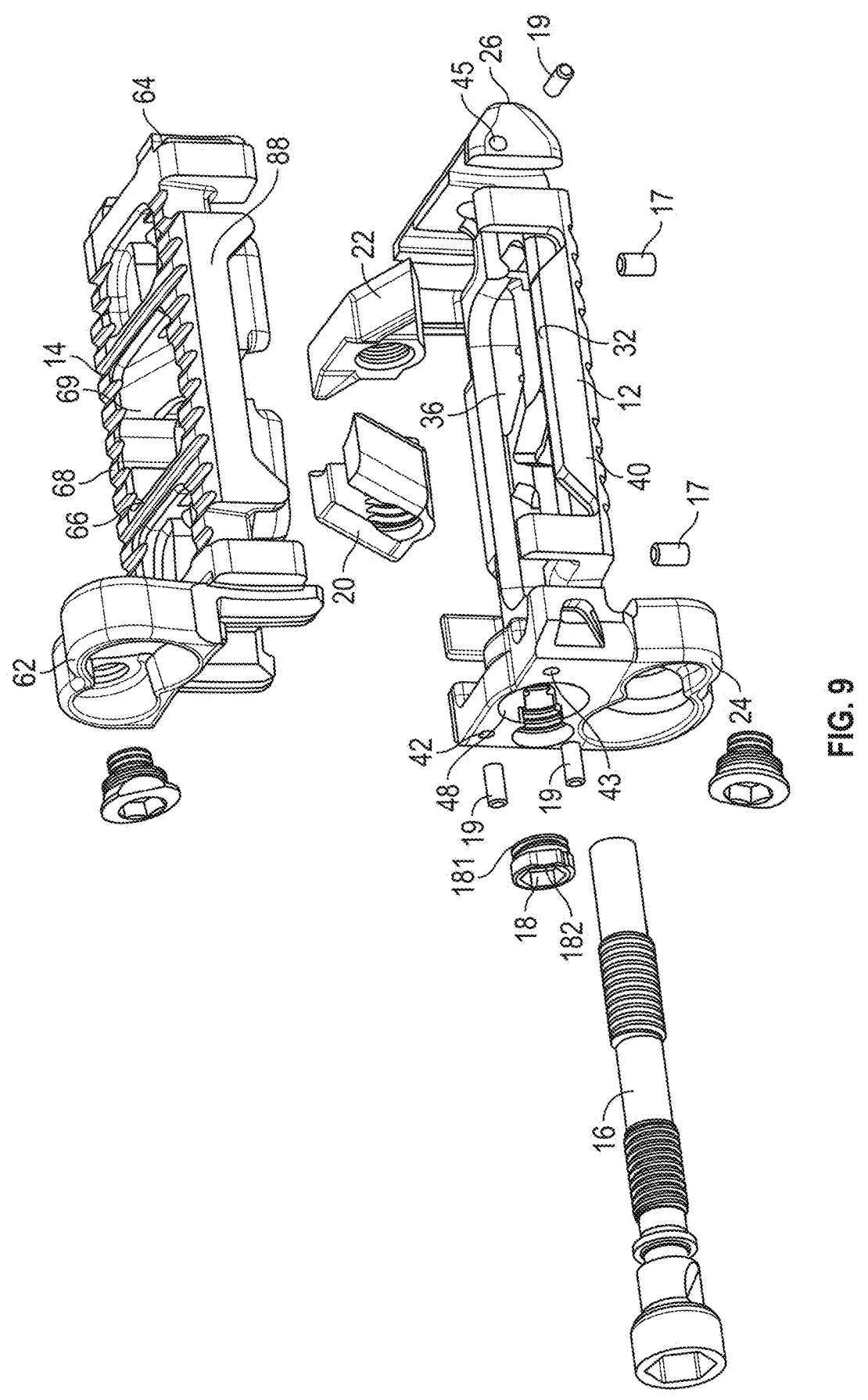
FIG. 9 is an exploded view of the implant of FIG. 1 according to an example embodiment.

Once the implant 10 is positioned within a desired space and expanded to a desired degree of expansion, the control shaft 16 can be secured using a cam screw 18. The cam screw 18 includes a threaded shaft 181 and a head 182, as shown in FIG. 9. The threaded shaft 181 allows the cam screw 18 to be screwed into the base member 12. The head 182 includes a tool port 184. The tool port 184 allows the cam screw to be tightened or loosened using a tool, such as a hex head driver. While this example embodiment shows the hex head tool port 184, it should be appreciated that the tool port 184 can be designed to receive several different types of hand tools, including a slotted screw driver, a Phillips-head screwdriver, an Allen wrench screwdriver, a hexagonal drive, a torx drive, a Robertson drive, a tri-wing screwdriver, an Allen security driver, a torx security driver, a Pozidriv, a clutch drive, a spanner, a Schrader drive, a nut driver, a hex wrench, a node security driver, any combination of the listed driver interfaces, and any other type of driver interface.

Figure 25:
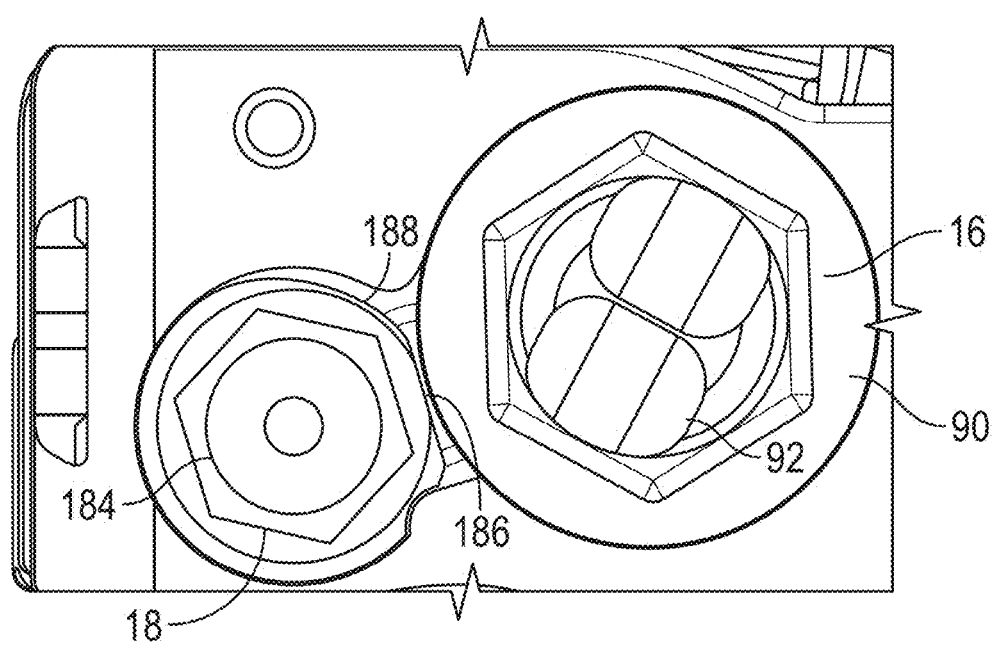
FIG. 25 is a front view of a control shaft and cam screw according to an example embodiment.
Figure 26:
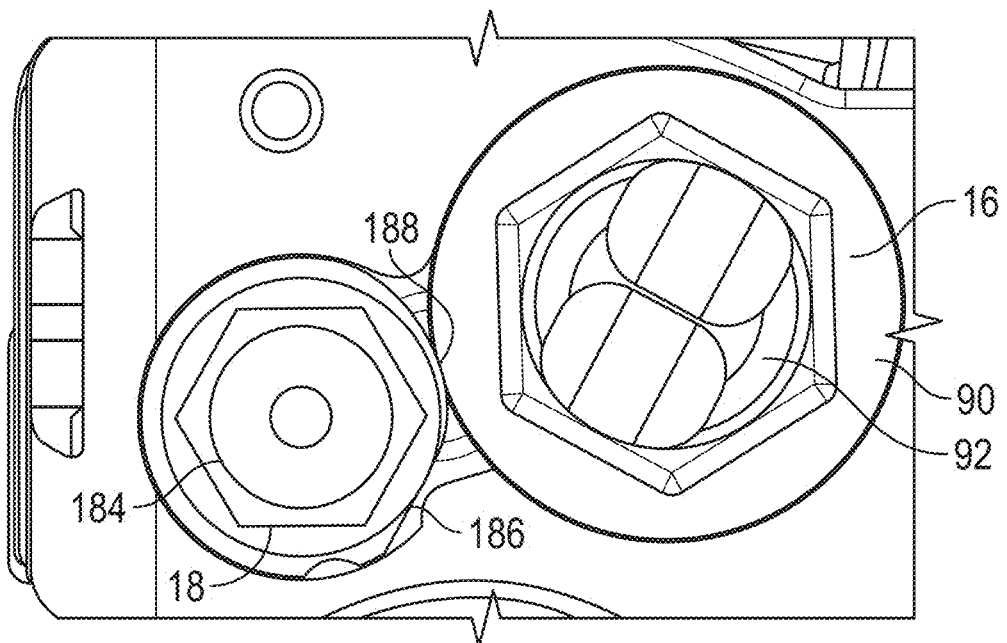
FIG. 26 is a front view of a control shaft and cam screw of the implant of FIG. 21 according to an example embodiment.

The head 182 further includes a flat portion 186 and a cam portion 188, as shown in FIGS. 25 and 26. The flat portion 186 includes a flat edge at the edge of the head 182, and the cam portion 188 includes a rounded edge with an increasing radius (e.g. the radius of the circular arc which best approximates the curve of the guide groove at that point) in the counter-clockwise direction.

In an example embodiment, when the implant 10 is in a collapsed position, the flat portion 186 of the cam screw 18 may be proximate to the control shaft 16, as shown in FIG. 25. Once the implant 10 is positioned within a desired space and expanded to a desired degree of expansion, the control shaft 16 may be locked into position by turning the cam screw 18. For example, the cam screw 18 may be tightened such that the cam portion 188 engages, and is in contact with, the head 90 of the control shaft, as shown in FIG. 26. In doing so, the force applied by the cam portion 188 of the cam screw 18 to the head 90 of the control shaft 16 may assist in preventing the control shaft 16 from rotating, thereby locking the control shaft 16 into position.

In some example embodiments, the cam screw 18 may further be configured to lock the control shaft 16 into place. In one example, after the implant 10 is installed, the implant 10 may be prone to over-expanding. In this example, as the implant 10 expands, the control shaft 16, as shown in FIG. 26, will turn in a counter-clockwise direction. In this example, the cam screw 18 may be threaded using a right-hand configuration, wherein turning the cam screw 18 in a clockwise direction will tighten the cam screw 18 into the base member 12 of the implant 10. In this example, the cam portion 188 is engaged with the head 90 of the control shaft 16. If the control shaft 16 begins to rotate in a counter-clockwise direction, the friction between the cam portion 188 and the head 90 will cause the cam screw 18, as shown in FIG. 25, to turn in a clockwise direction, further tightening the cam screw 18, which will further lock the control shaft 16 into position.

Additionally, in the example that the implant 10 is prone to over-expanding, a plurality of retention pins 19 may be utilized to prevent over-expansion. For example, as shown in FIG. 1, a retention pin 19 may be press fit into the first pin aperture 42, extending into the first pin slot 82 (see FIG. 10). In this example, when the implant 10 is in the fully expanded position, the retention pin 19 may bottom out against the bottom of the first pin slot 82, preventing the implant 10 from further expanding. Similarly, a retention pin 19 may be press fit into the second pin aperture 43, extending into the second pin slot 83. In this example, when the implant 10 is in the fully expanded position, the retention pin 19 may bottom out against the bottom of the second pin slot 83, preventing the implant 10 from further expanding. Further, a retention pin 19 may be press fit into the third pin aperture, extending into the third pin slot. In this example, when the implant 10 is in the fully expanded position, the retention pin 19 may bottom out against the bottom of the third pin slot, preventing the implant 10 from further expanding. Additionally, a retention pin 19 may be press fit into the fourth pin aperture 45, extending into the fourth pin slot 84. In this example, when the implant 10 is in the fully expanded position, the retention pin 19 may bottom out against the bottom of the third pin slot, preventing the implant 10 from further expanding.

Additionally, the expansion profile of the implant 10 may be further customized by varying the length of the pin slots 82, 83, 84. As discussed above, when a pin 19 is inserted into a pin aperture 42, 43, 45 and into a pin slot 82, 83, 84, the pin 19 may bottom out against the bottom of the pin slot 82, 83, 84, thereby preventing the implant 10 from over expanding. As shown in FIG. 10, the first pin slot 82 is longer than the second pin slot 83. Therefore, when the pins 19 are bottomed out against the bottom of the pin slots 82, 83, such as the embodiment shown in FIG. 5, the first lateral side portion 86 will be able to expanded a greater distance than the second lateral side portion 88.

In another example embodiment, after the implant 10 is installed, the implant 10 may be prone to collapsing. In this example, as the implant 10 collapses, the control shaft 16, as shown in FIG. 25, will turn in a clockwise direction. In this example, a cam screw 18 may be threaded using a left-hand configuration, wherein turning the cam screw 18 in a counter-clockwise direction will tighten the cam screw 18 into the base member 12 of the implant 10. Further, the cam screw 18 will include a cam portion 188 that will increase in radius (e.g. the radius of the circular arc which best approximates the curve of the guide groove at that point) in the clockwise direction. In this example, the cam portion 188 is engaged with the head 90 of the control shaft 16. If the control shaft 16 begins to rotate in a clockwise direction, the friction between the cam portion 188 and the head 90 will cause the cam screw 18 to turn in a counter-clockwise direction, further tightening the cam screw 18, which will further lock the control shaft 16 into position.

It should be noted that the implant 10 may share various features with the other implants described herein, and be made of the same, similar, or different materials. For example, various components of the implant 10 may be made of metal, plastic, composites, or other suitable biocompatible materials. Further, the implant 10 may be usable in connection with the spine or other parts of the body.

Figure 21:
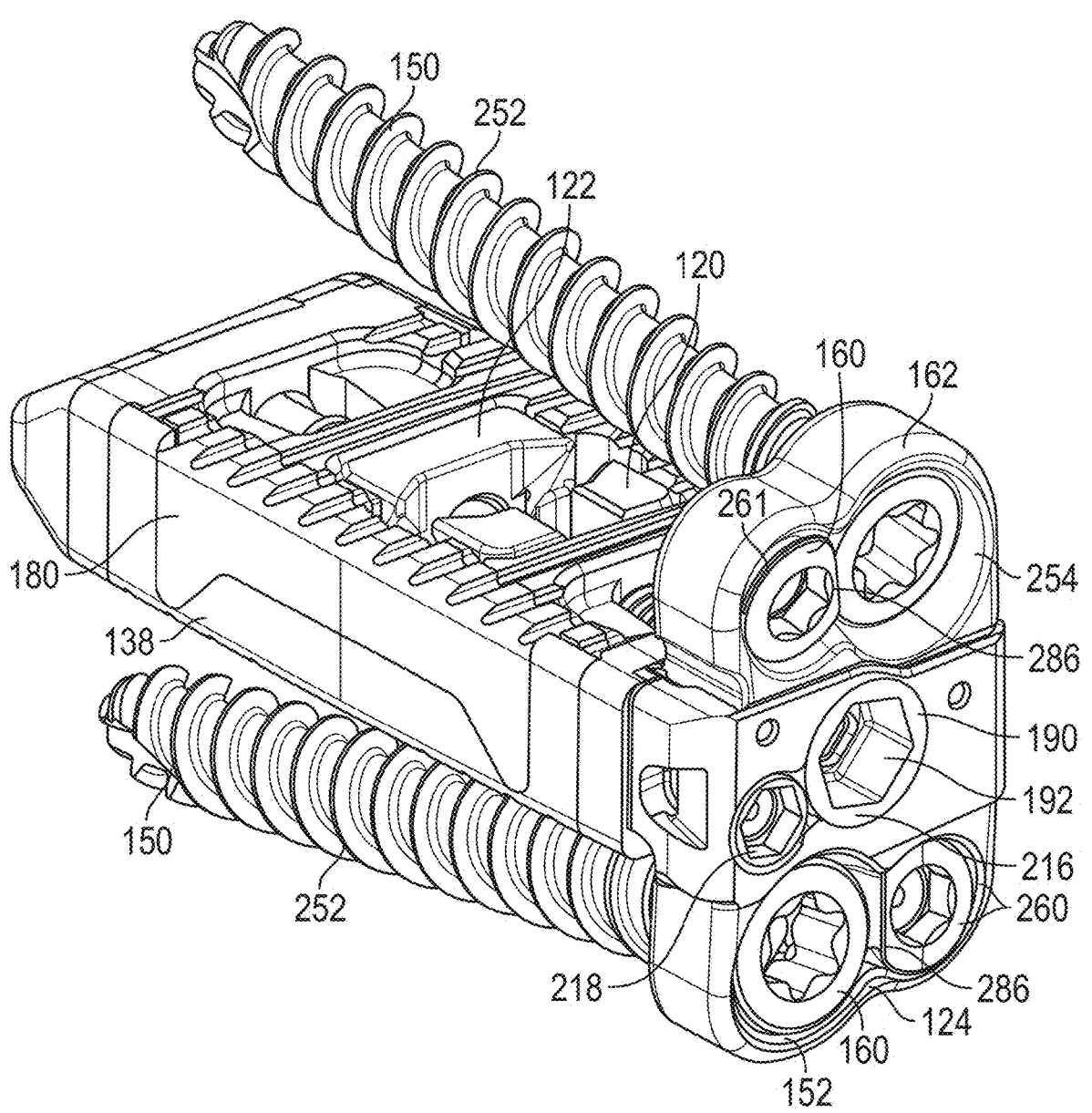
FIG. 21 is a perspective view of an implant according to another example embodiment.
Figure 22:
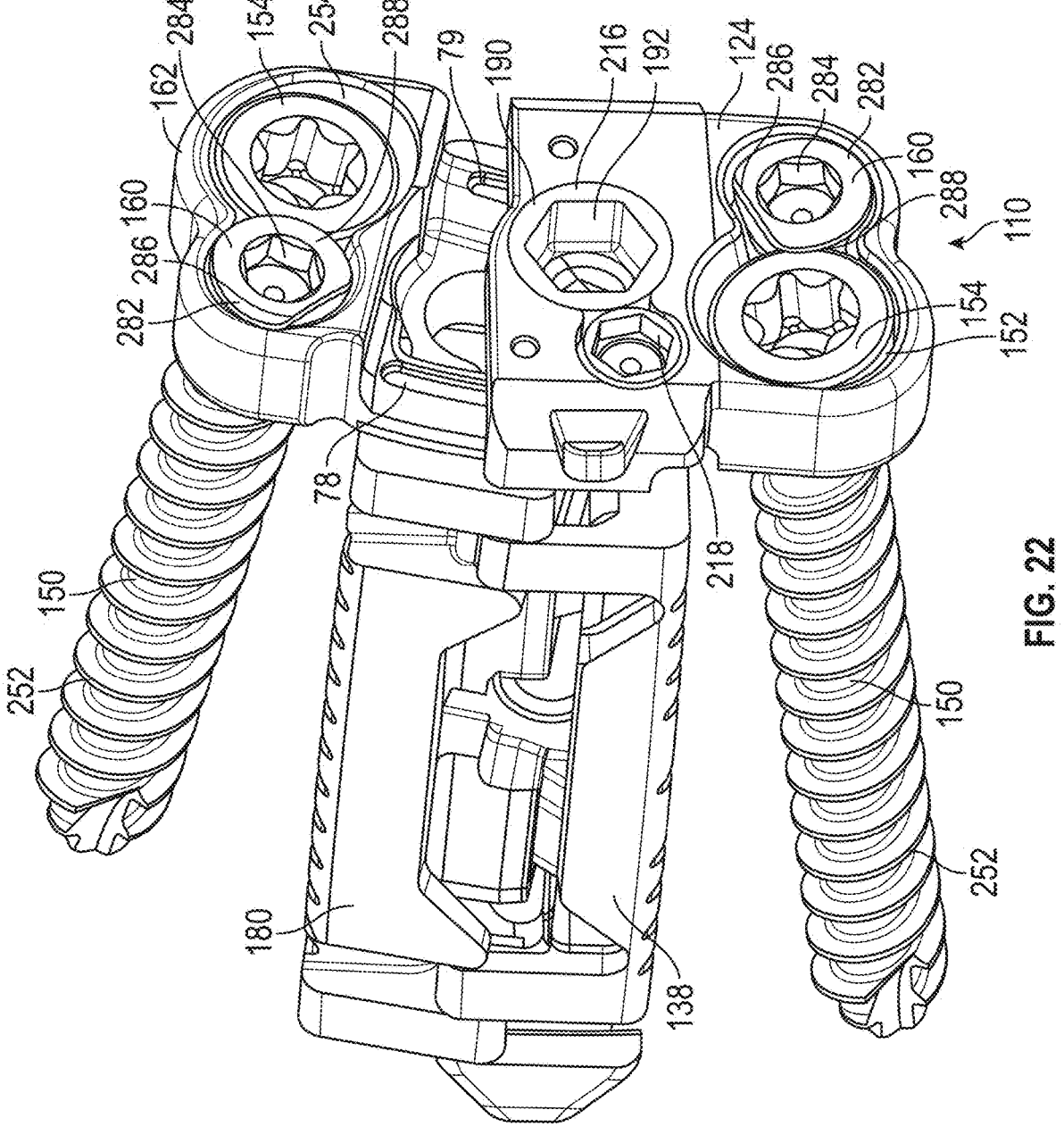
FIG. 22 is a perspective view of the implant of FIG. 21 according to an example embodiment.
Figure 23:
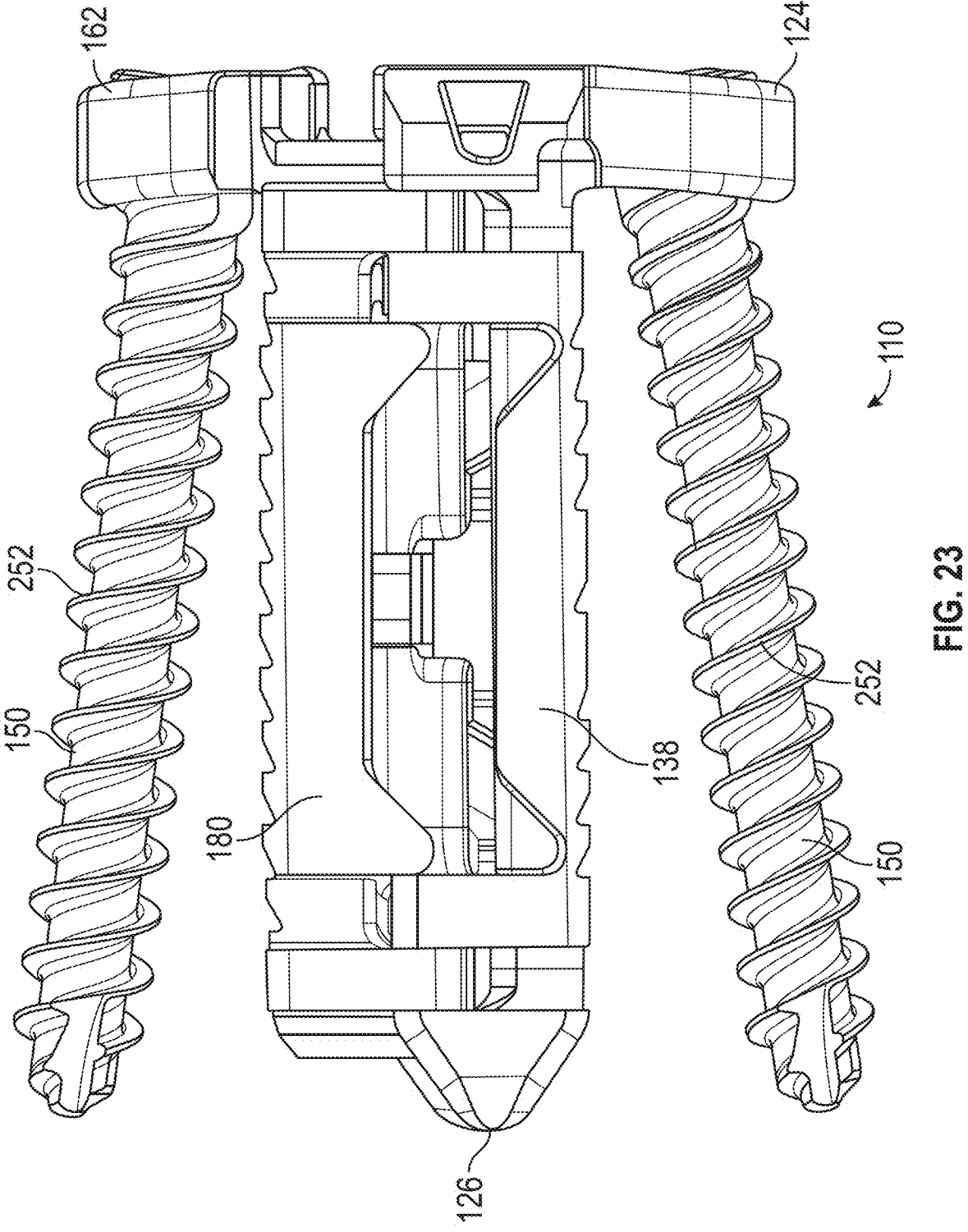
FIG. 23 is a side view of the implant of FIG. 21 according to an example embodiment.

Referring now to FIGS. 21-23, in some embodiments, one or both of a base member 112 and an adjustable member 114 of an implant 110 may be configured to receive an anchoring member to further secure the implant 110 to adjacent portions of bone. In an example embodiment, the anchoring member may be a bone screw 150. For example, as shown in FIGS. 21 and 22, an implant 110 includes a base member 112 and an adjustable member 114 adjustably coupled to the base member 112. A control shaft 216 is received by the base member 112 and is retained by a cam screw 218 passing through a portion of the base member 112. A first control member 120 and a second control member 122 are received on the control shaft 216 and are movable along the control shaft 216 to adjust a position of the adjustable member 114 between a collapsed position, as shown in FIG. 21 and an expanded position, as shown in FIGS. 22 and 23. Bone screws 150 extend through base member 112 and adjustable member 114.

In some embodiments, implant 110 may share any combination of the features disclosed herein with respect to the other implants, and all such combinations of features are to be understood to be within the scope of the present disclosure. In some embodiments, the implant 110 is substantially similar to implant 10, except as described herein. In an example embodiment, the base member 112 includes a first bone screw bore 152 configured to receive bone screw 150. Similarly, the adjustable member 114 includes a second bone screw bore 254 configured to receive bone screw 150. In some embodiments, the first bone screw bore 152 is integrated into the base member 112. In some embodiments, the second bone screw bore 254 is integrated into the adjustable member 114.

According to the example embodiment shown in FIGS. 21-23, the bone screw 150 includes a linear, externally threaded shaft 252, a head 154 at a first end, and a tip 156 at a second end opposite the first end. In some embodiments, the tip 156 is pointed. In some embodiments, the diameter of the bone screw 416 remains constant from the head 154 to the tip 156. The head 154 further includes a socket 158 that is configured to receive an installation tool. While this example embodiment has a torx drive socket 158, it should be appreciated that the socket 158 can be designed to receive several different types of hand tools, including a slotted screw driver, a Phillips-head screwdriver, an Allen wrench screwdriver, a hexagonal drive, a torx drive, a Robertson drive, a tri-wing screwdriver, an Allen security driver, a torx security driver, a Pozidriv, a clutch drive, a spanner, a Schrader drive, a nut driver, a hex wrench, a node security driver, any combination of the listed driver interfaces, and any other type of driver interface.

Once the bone screw 150 is inserted into a bone, a retention screw 160 may be used to prevent a back-out of the bone screw 150. In an example embodiment, such as the embodiment shown in FIG. 24, the retention screw 160 may include a head 282, a tool port 284, and a threaded shaft. The threaded shaft may be screwed into a first threaded bore 260 in the base member 112 or into a second threaded bore 261 in the adjustable member 114, as shown in FIGS. 21-24. In some embodiments, the first threaded bore 260 is integrated into the base member 112. In some embodiments, the second threaded bore 261 is integrated into the adjustable member 114.

Figure 24:
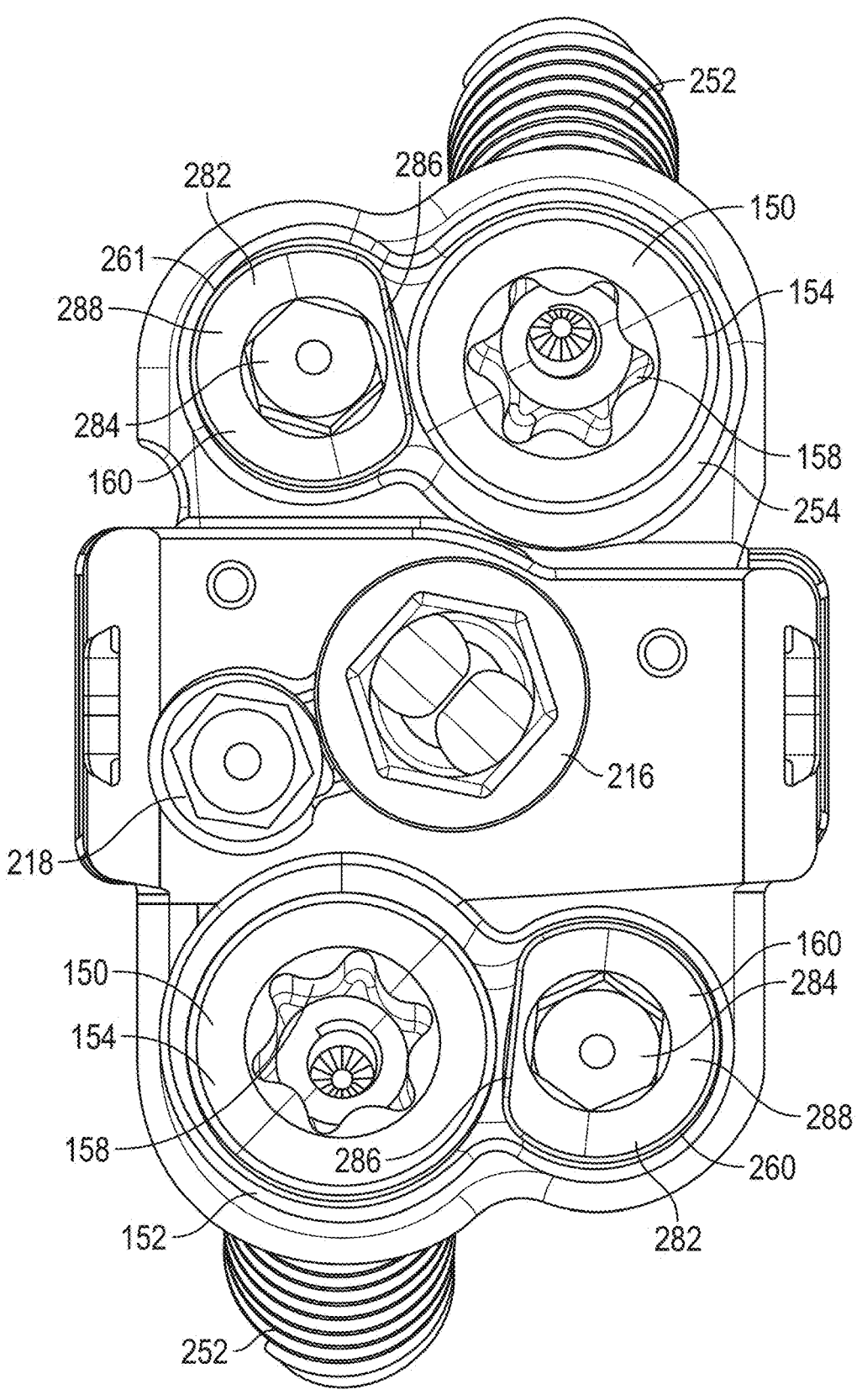
FIG. 24 is a front view of the implant of FIG. 21 according to an example embodiment.

The head 282 further includes a flat portion 286 and a rounded shoulder portion 288. In some embodiments, when the flat portion 286 is proximate the head 154 of the bone screw, the retention screw 160 is not in contact with the bone screw 150, as shown in FIG. 24. However, the retention screw 160 may be tightened into the first threaded bore 260 or the second threaded bore 261, such that the rounded shoulder portion 228 is proximate to the bone screw 150. In some embodiments, when the retention screw 160 is tightened into the first threaded bore 260 or second threaded bore 261, the underside of the rounded shoulder portion 228 is in contact with the head 154 of the bone screw 150. In doing so, the retention screw 160 may be used to prevent back out of the bone screw 150.

In the example embodiment shown in FIGS. 21-24, the retention screw 160 includes a tool port 284 configured to receive a hex head driver. It should be appreciated that the tool port 284 can be designed to receive several different types of hand tools, including a slotted screw driver, a Phillips-head screwdriver, an Allen wrench screwdriver, a hexagonal drive, a torx drive, a Robertson drive, a tri-wing screwdriver, an Allen security driver, a torx security driver, a Pozidriv, a clutch drive, a spanner, a Schrader drive, a nut driver, a hex wrench, a node security driver, any combination of the listed driver interfaces, and any other type of driver interface.

Referring now to the Figures generally, the various embodiments disclosed herein provide expandable implants including a base member, an adjustable member adjustably coupled to the base member and movable between a first, collapsed position, and a second, expanded position, and a control shaft rotatably received by the base member, where rotation of the control shaft causes relative movement of the adjustable member relative to the base member. At least one control member is received on the control shaft and by the control channel, and rotation of the control shaft causes the control member to translate along the control shaft and along the control channel.

In some embodiments, the top surface of the upper support and the bottom surface of the bottom support are parallel when the implant is in the first, collapsed position (see e.g., FIG. 1). However, in other embodiments, the top surface of the upper support and the bottom surface of the lower support may form an angle when the implant is in the first, collapsed position. In this example embodiment, the implant will have a larger height (i.e., the distance between the top surface of the upper support and the bottom surface of the lower support) on one lateral side of the implant than the other lateral side of the implant. In this embodiment, the implant may expand linearly (i.e., the angle remains constant as the implant expands), or the implant may angularly expand (i.e., the angle increases as the implant expands).

In some embodiments, the adjustable member moves in a linear fashion relative to the base member. In other embodiments, the adjustable member moves in a non-linear fashion relative to the base member. In further embodiments, the adjustable member pivots about a pivot axis relative to the base member. The pivot axis may be provided by a pivot pin extending through one or both of the adjustable member and the base member.

In some embodiments, a single control member and control channel are utilized. In other embodiments, multiple (e.g., 2) control members and control channels are utilized. In some embodiments, the multiple control channels are parallel and straight. In other embodiments, the control channels are non-parallel and straight (e.g., angled toward each other). In further embodiments, the control channels are non-parallel and non-straight such that the adjustable member moves in a non-linear fashion relative to the base member.

In some embodiments, the control shaft includes a control thread corresponding to each control member. As such, while in some embodiments the control shaft includes a single control thread, in other embodiments the control shaft includes multiple (e.g., first and second) control threads. In some embodiments, the control threads are like-threaded. In other embodiments, the control threads have different threads. For example, in some embodiments, a first control thread is opposite-handed from a second control thread. In further embodiments, a first control thread has a different pitch from a second control thread. In yet further embodiments, a first control thread is different handed and has a different pitch from a second control thread.

In some embodiments, one or both of the adjustable member and the base member include projections/grooves to provide a gripping surface intended to facilitate gripping adjacent portions of bone. In further embodiments, one or both of the adjustable member and the base member include one or more apertures and/or cavities configured to promote bone growth in and around the adjustable member and the base member. In some embodiments, the apertures extend from a top, bottom, and/or side surface of the adjustment member or the base member and to a central cavity of the implant.

According to any of the embodiments disclosed herein, one or more bone screws may be included and positioned to extend through one or both of the adjustable member and the base member and into adjacent portions of bone. In some embodiments, multiple bone screws are used. A first bone screw may extend through the adjustable member and into a first portion of bone, and a second bone screw may extend through the base member and into a second portion of bone. In further embodiments, multiple bone screws are accessible and manipulatable by way of the front face of the implant defined by one or both of the adjustable member and the base member. A head and tool port of the control shaft may further be accessible by way of the front face of the implant.

In various embodiments, any suitable configuration of the control shaft/control member(s)/control channel(s) may be utilized. In some embodiments, an at least partially spherical control member threadingly engages a threaded control shaft and translates both along the control shaft and within the control channel. In other embodiments, the control member is non-spherical and is received at least partially on or in a control rail or control channel provided by the adjustable member, such that the control member translates along both the control shaft and the control channel or control rail.

It is important to note that the construction and arrangement of the elements of the various implants and implant components as shown in the exemplary embodiments are illustrative only. Although a few embodiments have been described in detail in this disclosure, those skilled in the art who review this disclosure will readily appreciate that many modifications are possible (e.g., variations in sizes, dimensions, structures, shapes and proportions of the various elements, values of parameters, mounting arrangements, materials, colors, orientations, etc.) without materially departing from the novel teachings and advantages of the subject matter recited in the various embodiments. Accordingly, all such modifications are intended to be included within the scope of the present disclosure as defined in the appended claims. The order or sequence of any process or method steps may be varied or re-sequenced according to alternative embodiments. Other substitutions, modifications, changes, and/or omissions may be made in the design, operating conditions, and arrangement of the exemplary embodiments without departing from the spirit of the present disclosure.

As utilized herein, the terms "approximately," "about," "substantially", and similar terms are intended to have a broad meaning in harmony with the common and accepted usage by those of ordinary skill in the art to which the subject matter of this disclosure pertains. It should be understood by those of skill in the art who review this disclosure that these terms are intended to allow a description of some features described and claimed without restricting the scope of these features to the precise numerical ranges provided. Accordingly, these terms should be interpreted as indicating that insubstantial or inconsequential modifications or alterations of the subject matter described and claimed are considered to be within the scope of the application as recited in the appended claims.

It should be noted that the term "exemplary" as used herein to describe various embodiments is intended to indicate that such embodiments are possible examples, representations, and/or illustrations of possible embodiments (and such term is not intended to connote that such embodiments are necessarily extraordinary or superlative examples).

The terms "coupled," "connected," and the like as used herein mean the joining of two members directly or indirectly to one another. Such joining may be stationary (e.g., permanent) or moveable (e.g., removable or releasable). Such joining may be achieved with the two members or the two members and any additional intermediate members being integrally formed as a single unitary body with one another or with the two members or the two members and any additional intermediate members being attached to one another.

References herein to the positions of elements (e.g., "top," "bottom," "above," "below," etc.) are merely used to describe the orientation of various elements in the FIGURES. It should be noted that the orientation of various elements may differ according to other exemplary embodiments, and that such variations are intended to be encompassed by the present disclosure.

Although the figures and description may illustrate a specific order of method steps, the order of such steps may differ from what is depicted and described, unless specified differently above. Also, two or more steps may be performed concurrently or with partial concurrence, unless specified differently above. Such variation may depend, for example, on hardware systems chosen and on designer choice. All such variations are within the scope of the disclosure.

It is important to note that the construction and arrangement of the various exemplary embodiments are illustrative only. Although only a few embodiments have been described in detail in this disclosure, those skilled in the art who review this disclosure will readily appreciate that many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter described herein. For example, elements shown as integrally formed may be constructed of multiple parts or elements, the position of elements may be reversed or otherwise varied, and the nature or number of discrete elements or positions may be altered or varied. The order or sequence of any process or method steps may be varied or re-sequenced according to alternative embodiments. Other substitutions, modifications, changes and omissions may also be made in the design, operating conditions and arrangement of the various exemplary embodiments without departing from the scope of the present application.

It should be appreciated that dimensions of the components, structures, and/or features of the present implants and installation instruments may be altered as desired within the scope of the present disclosure.

What is claimed is:

1. An expandable implant comprising:

a base member having a bottom surface and an end extending from the bottom surface, the end comprising at least one curved guide groove extending from the bottom surface;

an adjustable member adjustably coupled to the base member and movable between a first, collapsed position, and a second, expanded position, wherein the adjustable member has a top surface and an end extending from the top surface, the end comprising at least one curved guide rail extending from the top surface, wherein the at least one curved guide rail translates within the at least one curved guide groove as the adjustable member moves between the first, collapsed position, and the second, expanded position;

a first lateral side extending along a length of the expandable implant and having a first height defined by the top surface of the adjustable member and the bottom surface of the base member proximate the first lateral side;

a second lateral side opposite the first lateral side, extending along the length of the expandable implant and having a second height defined by the top surface of the adjustable member and the bottom surface of the base member proximate the second lateral side;

wherein a change in the first height proximate the first lateral side is different than a change in the second height proximate the second lateral side when the expandable implant is moved from the first, collapsed position to the second, expanded position, and wherein the change in the first height at the first lateral side and the change in the second height at the second lateral side are each greater than zero.

2. The expandable implant of claim 1, wherein the first height proximate the first lateral side is substantially equal to the second height proximate the second lateral side when the expandable implant is in the first, collapsed position.

3. The expandable implant of claim 1, further comprising a control assembly comprising a control shaft and a control member threadingly received on the control shaft, and wherein rotation of the control shaft causes relative movement of the adjustable member relative to the base member.

4. The expandable implant of claim 3, wherein the control member comprises a first control member received on the control shaft and configured to be received within a first control channel on the adjustable member.

5. The expandable implant of claim 4, wherein the control member comprises a second control member received on the control shaft and configured to be received within a second control channel on the adjustable member.

6. The expandable implant of claim 5, wherein the first control member moves towards the second control member along the control shaft in response to the control shaft being turned in a first direction; and wherein the first control member moves away from the second control member along the control shaft in response to the control shaft being turned in a second direction.

7. The expandable implant of claim 3, wherein the control shaft is secured using a cam screw, and wherein the cam screw has a cam portion configured to engage the control shaft.

8. The expandable implant of claim 1, wherein the base member comprises at least one aperture and the at least one curved guide rail comprises a slot extending into the curved guide rail, wherein the aperture and the slot are configured to receive a retention pin to guide movement of the adjustable member.

9. The expandable implant of claim 1, wherein the at least one curved guide groove includes two curved guide grooves and the at least one curved guide rail includes two curved guide rails, wherein one curved guide groove and one curved guide rail are positioned proximate the first lateral side and the other of the curved guide groove and the other of the curved guide rail are positioned proximate the second lateral side.

10. An expandable implant comprising:

a first member having a bottom surface and an end extending from the bottom surface, the end comprising at least one curved guide groove extending from the bottom surface;

a second member adjustably coupled to the first member and movable between a first, collapsed position, and a second, expanded position, wherein the second member has a top surface and an end extending from the top surface, the end comprising at least one curved guide rail extending from the top surface, wherein the at least one curved guide rail translates within the at least one curved guide groove as the second member moves between the first, collapsed position, and the second, expanded position;

wherein the second member moves in a non-linear manner relative to the first member from the first, collapsed position to the second, expanded position such that a change in a height proximate a first lateral side of the expandable implant is different than a change in a height proximate a second lateral side of the expandable implant opposite the first lateral side, and wherein the change in the height at the first lateral side and the change in the height at the second lateral side are each greater than zero.

11. The expandable implant of claim 10, wherein the first member comprises a top surface opposite the bottom surface;

wherein the second member has a bottom surface opposite the top surface; and wherein the bottom surface of the first member is substantially parallel to the top surface of the second member in the first, collapsed position.

12. The expandable implant of claim 11, wherein the bottom surface of the first member forms a first angle with the top surface of the second member in the second, expanded position, wherein the first angle is greater than 0 degrees.

13. The expandable implant of claim 10, further comprising a control assembly comprising a control shaft and a control member, wherein rotation of the control shaft causes relative movement of the second member relative to the first member.

14. The expandable implant of claim 13, wherein the control member comprises a first control member received on the control shaft and configured to be received within a first control channel on the second member.

15. The expandable implant of claim 14, further comprising a second control member received on the control shaft and configured to be received within a second control channel on the second member.

16. The expandable implant of claim 15, wherein the first control member moves towards the second control member along the control shaft in response to the control shaft being turned in a first direction; and wherein the first control member moves away from the second control member along the control shaft in response to the control shaft being turned in a second direction.

17. An expandable implant comprising:

a base member comprising a first body portion defining a bottom surface and an end extending from the bottom surface, and a first transverse plate portion configured to receive a first anchoring member, the end comprising at least one curved guide groove extending from the bottom surface;

an adjustable member comprising a second body portion defining a top surface and an end extending from the top surface, and a second transverse plate portion configured to receive a second anchoring member, wherein the adjustable member is adjustably coupled to the base member, and wherein the adjustable member moves non-linearly with respect to the base member between a first position and a second position, and where the end comprises at least one curved guide rail extending from the top surface, wherein the at least one curved guide rail translates within the at least one curved guide groove as the adjustable member moves between the first, collapsed position, and the second, expanded position; and a control assembly configured to cause movement of the adjustable member relative to the base member;

wherein a change in a height proximate a first lateral side of the expandable implant is different than a change in a height proximate a second lateral side of the expandable implant opposite the first lateral side, and wherein the change in the height proximate the first lateral side and the change in the height proximate the second lateral side are each greater than zero.

18. The expandable implant of claim 17, wherein the top surface of the adjustable member and the bottom surface of the base member define an implant height; and wherein the implant height proximate the first lateral side is greater than the implant height proximate the second lateral side when the expandable implant is in the second position.

19. The expandable implant of claim 18, wherein the top surface of the adjustable member and the bottom surface of the base member are substantially parallel in the first position.

20. The expandable implant of claim 17, wherein the control assembly includes a first control member received on a control shaft and configured to be received within a first control channel on the adjustable member.

21. The expandable implant of claim 17, wherein the first anchoring member is secured using a retention screw.

22. The expandable implant of claim 21, wherein the retention screw has a flat portion and a rounded shoulder portion.

* * * * *